United States Patent

Nakazawa

[11] Patent Number: 5,981,968
[45] Date of Patent: Nov. 9, 1999

[54] RADIOGRAPHIC IMAGE READING APPARATUS AND A RADIOGRAPHIC IMAGE INFORMATION READING METHOD

[75] Inventor: Masayuki Nakazawa, Tokyo, Japan

[73] Assignee: Konica Corporation, Tokyo, Japan

[21] Appl. No.: 08/695,319

[22] Filed: Aug. 9, 1996

[30] Foreign Application Priority Data

Aug. 15, 1995 [JP] Japan .................................. 7-208175

[51] Int. Cl.⁶ .................................................. G03B 42/02
[52] U.S. Cl. ................................................... 250/587
[58] Field of Search ......................................... 250/587

[56] References Cited

U.S. PATENT DOCUMENTS

| | | | |
|---|---|---|---|
| 3,859,527 | 1/1975 | Luckey . | |
| 4,755,672 | 7/1988 | Watanabe et al. | 250/587 |
| 5,006,708 | 4/1991 | Itoh et al. | 250/587 |

FOREIGN PATENT DOCUMENTS

| | | |
|---|---|---|
| 55-12144 | 1/1980 | Japan . |
| 60-234643 | 11/1985 | Japan . |
| 63-158536 | 7/1988 | Japan . |

*Primary Examiner*—Constantine Hannaher
*Attorney, Agent, or Firm*—Frishauf, Holtz, Goodman, Langer & Chick, P.C.

[57] ABSTRACT

A method of reading a radiographic image on a stimulable phosphor sheet includes a step of obtaining correction data in which a spatial frequency processing is conducted so as to reduce a predetermined spatial frequency component of an image information which is irradiated with radiation without placing a subject. The predetermined spatial frequency component corresponds to an irregularity with poor reproducibility in terms of its position on the image information. The correction data is made so as to eliminate an irregularity which is reproducible of its position on the image information.

4 Claims, 27 Drawing Sheets

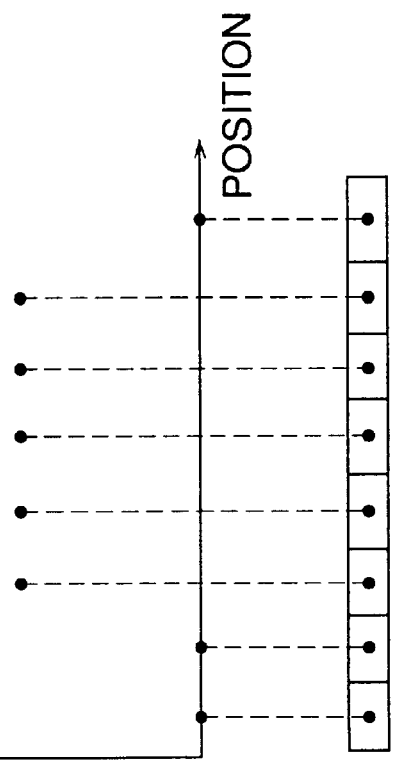

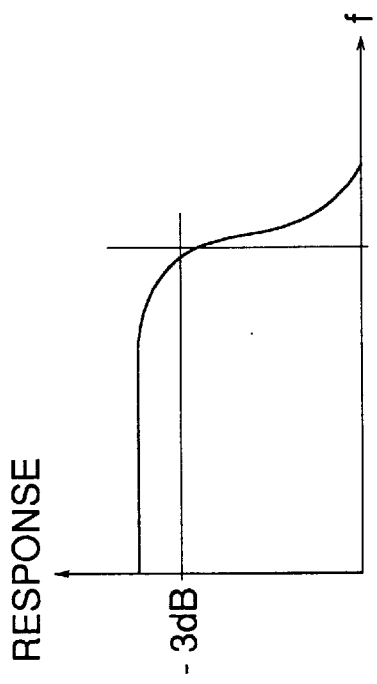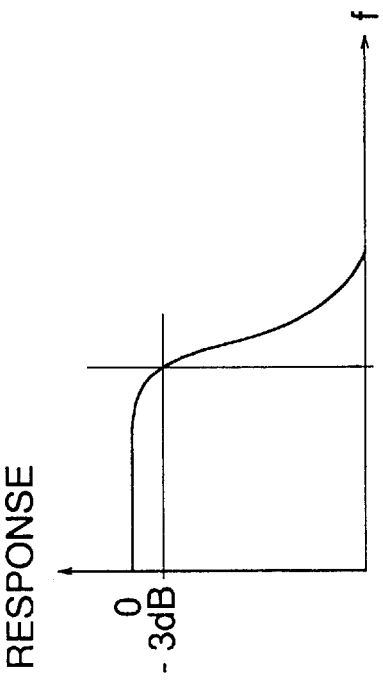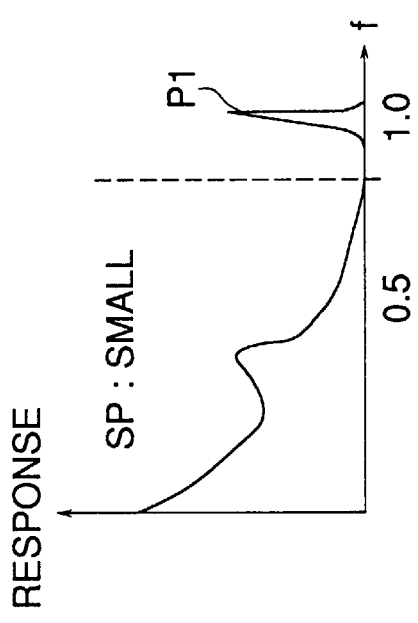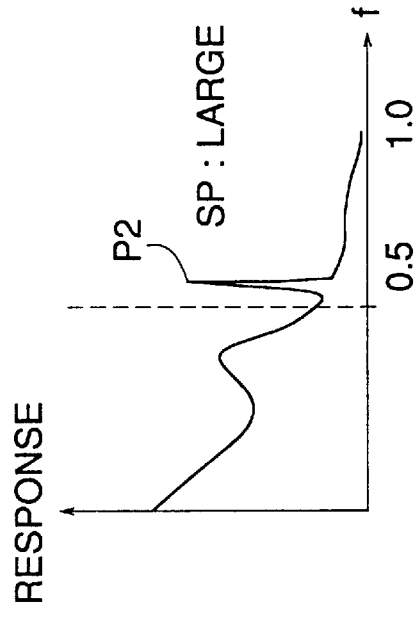
FIG. 12 (a)  FIG. 12 (b)  FIG. 12 (c)  FIG. 12 (d)

PRIOR ART
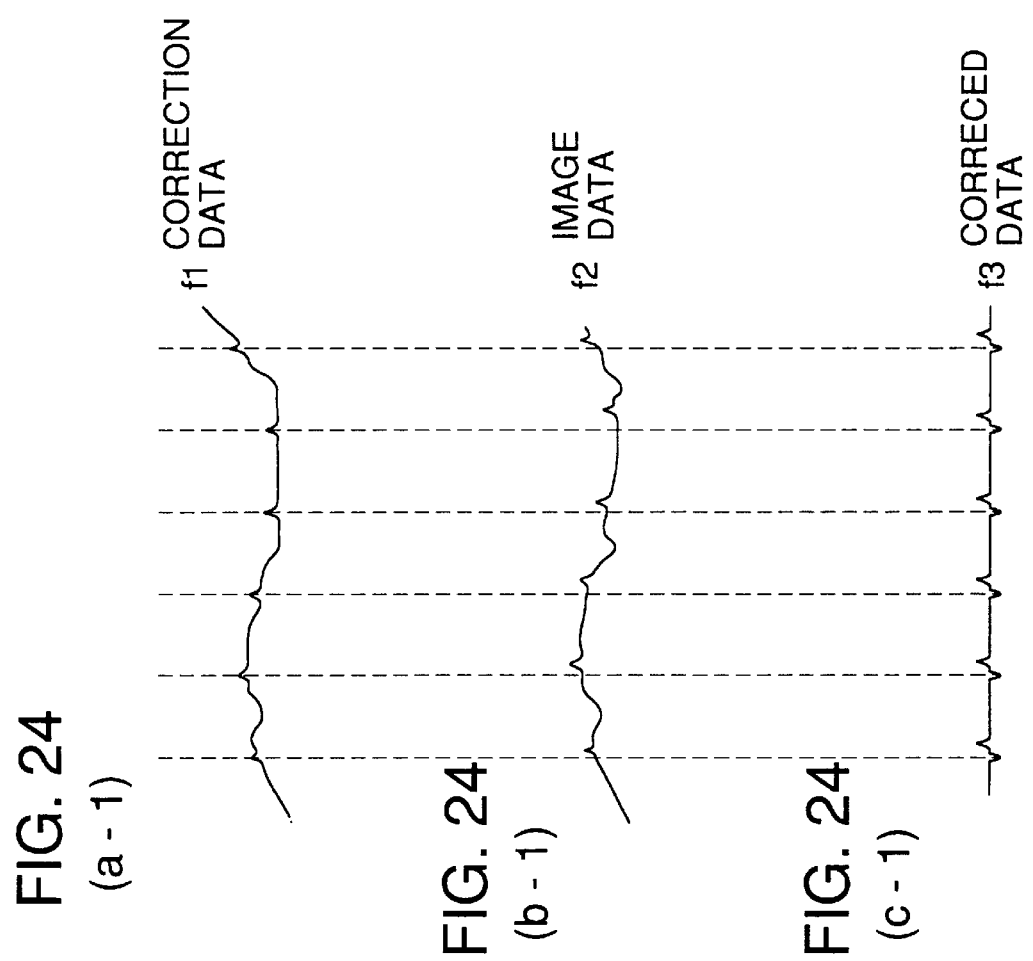

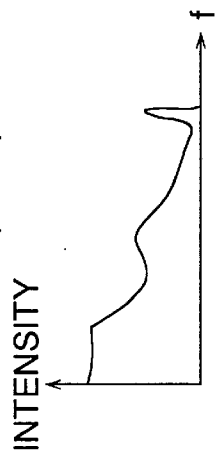
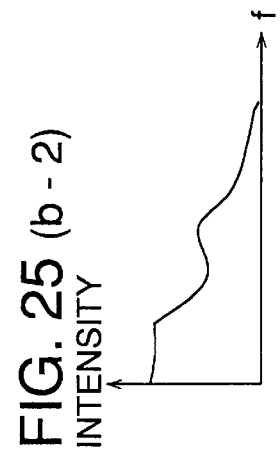
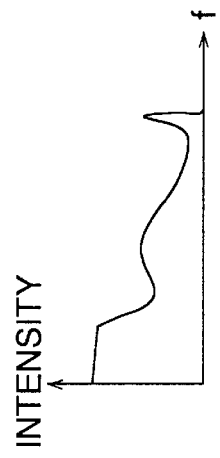
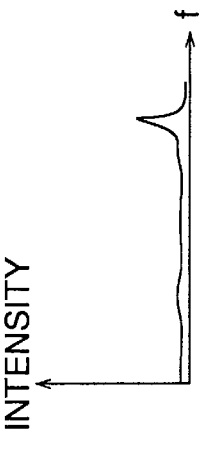
FIG. 25 (a-2) INTENSITY
FIG. 25 (b-2) INTENSITY
FIG. 25 (c-2) INTENSITY
FIG. 25 (d-2) INTENSITY
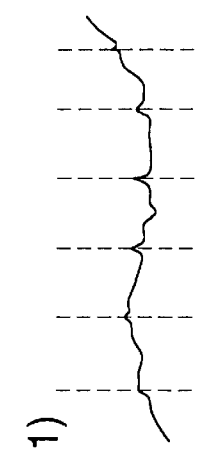
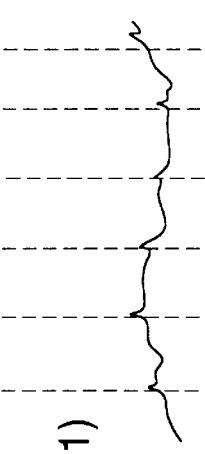
FIG. 25 (a-1) f1 CORRECTION DATA BEFORE PROCESSING
FIG. 25 (b-1) f2 CORRECTION DATA AFTER PROCESSING
FIG. 25 (c-1) f3 IMAGE DATA
FIG. 25 (d-1) f4 DATA AFTER CORRECTION

RADIOGRAPHIC IMAGE READING APPARATUS AND A RADIOGRAPHIC IMAGE INFORMATION READING METHOD

BACKGROUND OF THE INVENTION

The present invention relates to a radiographic image information reading method and a radiographic image reading apparatus, and in particular, to correction of an image to be read.

Recently, there has been devised a method for obtaining radiographic image information without using a radiographic film composed of a silver halide light-sensitive material. According to one such method, radiation transmitted through a subject is absorbed in a phosphor of a certain kind, and then the phosphor is excited by light or heat energy, for example, so that radiation energy accumulated in the phosphor through the aforesaid absorption is emitted as a fluorescence which is detected to be an image. To be concrete, for example, U.S. Pat. No. 3,859,527 and Japanese Patent Publication Open to Public Inspection No. 12144/1980 (hereinafter referred to as Japanese Patent O.P.I. Publication) disclose methods employing a radiographic image conversion panel and showing a radiographic image conversion method with excitation light of visible light or infrared radiation wherein a radiographic image conversion panel in which a stimurable phosphor layer is formed on a support is used. Radiation transmitted through a subject is projected on the accelerating phosphor layer of the radiographic image conversion panel so that radiation energy corresponding to radiation transmittance on each part of the subject is accumulated to form a latent image. Then, the accelerating phosphor layer is scanned by the aforesaid exciting light so that radiation energy accumulated on each part of the panel is emitted to be converted to light, and then, its intensity is detected by a photoelectric transfer element such as a photomultiplier or a photodiode to obtain a radiographic image.

FIG. 19 is an illustration showing how an image is recorded on a stimurable phosphor like that explained above. In the drawing, X-rays emitted from X-ray source 1 are narrowed down by diaphragm 2, and then are projected on subject 3. X-rays transmitted through the subject 3 enter accelerating phosphor 4 wherein a latent image of an image of the subject 3 is formed.

FIG. 20 is a block diagram showing a structural example of a conventional radiographic image information reading apparatus which reads radiographic images recorded on an accelerating phosphor in the manner explained above. The numeral 101 is a semi-conductor laser light source for generating exciting light, and the semi-conductor laser light source 101 is driven by laser driver circuit 102 in the form of pulses in synchronization with an image clock signal from image clock generator 125. Laser beam LB generated from the semi-conductor laser light source 101 arrives at deflector 107 through monochromatic light filter 103, mirror 104, beam-forming optical system 105 and mirror 106. The deflector 107 is equipped with polygon mirror 109 driven by deflector driver 108, and it deflects the laser beam LB to cover a certain angle in the scanning area. The deflected laser beam LB is adjusted to be at a constant speed on a scanning line, and it scans on radiographic image conversion panel 111 employing a stimurable phosphor as a radiographic image information recording medium in the direction of arrow "a" through mirror 110. The radiographic image conversion panel 111 moves simultaneously in the sub-scanning direction (direction of arrow "b"), and thereby an overall surface can be scanned. Light emitted from the radiographic image conversion panel 111 after scanning by the laser beam LB are converged by converging means 112 and arrive, through filter 113 transmitting only a wavelength range of the light, at light detector 114 provided with a photomultiplier where the light are converted to analog electric signals (image signals).

The numeral 115 is a power supply which supplies high voltage to the light detector 114 (photomultiplier). An image signal outputted as an electric current from the light detector 114 passes through front end amplifier 116 to be voltage-amplified, and further passes through logarithmic amplifier 118 that converts radiation intensity signals into image density signals, filter 119 and sample hold circuit 120 that holds signals for a certain period in synchronization with image clock signals, and then is converted into a digital signal by A/D converter 121 to be sent to an external data processing apparatus through interface 124.

In the case of reading radiographic image information, however, there have been problems such as sensitivity irregularity of radiations and accelerating phosphors (irregularity in both main- and sub-scanning directions), irregularity of exciting light scanning system and light converging system (irregularity in main-scanning direction) and an influence of a change with age of a stimurable phosphor (irregularity in the sub-scanning direction). As a technology for overcoming the aforesaid problems, there has been a correction technology described in Japanese Patent O.P.I. Publication No. 234643/1985.

However, in the technology described in the aforesaid patent, correction data for correcting the data read have been needed to be prepared for all pixels of a radiographic image conversion panel. Therefore, the capacity of a memory for the storage of correction data needs to be increased. When using a plurality of radiographic image conversion panels, in particular, memory capacity is increased in proportion to the number of panels, which is not preferable in practical use.

For solving the problems mentioned above, the present inventor proposed a novel method and a novel apparatus for reading radiographic image information (Japanese Patent O.P.I. Publication No. 158536/1988). According to this invention, correction data in a form of a line in the main-scanning direction and/or the sub-scanning direction are obtained from a solid image obtained through photographing without a subject and stored, and they are used for correcting image data in the case of photographing an image with a subject arranged. It is possible to save memory capacity greatly by having at least one list of correction data in the form of a line or a row without having correction data with total pixels two-dimensionally. Further, when obtaining correction data in the main-scanning direction or in the sub-scanning direction, it is possible to eliminate an influence of noise by averaging data of plural lines or rows.

In the invention, however, when streak-shaped noise (irregularity without position repeatability or an irregularity with poor reproducibility in terms of its position on an image) caused by vibration or irregularity of intervals on a polygon mirror appears on an image without a subject in the case of preparing correction data, the correction data can not be free from this influence. When image data is corrected by the use of correction data having the noise, the noise appears on the corrected image. As a cause of irregularity without position repeatability, there are irregularity in a light converging system and irregularity in an exciting light scanning system (defect and dust) for the main-scanning direction, and there are relative displacement (stationary vibration and shock from the outside) between a radiographic image conversion panel and a reading system, irregularity in an inclination angle of a polygon mirror and irregularity of reflection factor in mirror surfaces for the sub-scanning direction. With regard to such irregularity without repeatability, there have been some cases where the irregularity was increased when it was corrected.

FIGS. 24(a-1) to 24(c-2) are illustrations of some problems in conventional technologies. In the drawing, f1 in FIG. 24(a-1) represents correction data, FIG. 24(a-2) is a frequency spectrum of f1, f2 in FIG. 24(b-1) represents image data, FIG. 24(b-2) is a frequency spectrum of f2, and f3 in FIG. 24(c-1) represents image data after correction and FIG. 24(c-2) is a frequency spectrum of f3. The axis of ordinate for f1–f3 represents a size of image data, the axis of abscissa represents a position, and the axis of ordinate for a frequency spectrum represents intensity, and the axis of abscissa represents a spatial frequency. An example shown in the drawing indicates an occasion wherein irregularity having position repeatability at a relatively gentle change and irregularity having no position repeatability appearing at a constant cycle at a relatively abrupt change are mixed. Since the irregularity having position repeatability appears similarly on correction data f1 and image data f2, effective correction is made on image data f3 after correction. On the other hand, irregularity having no position repeatability appears differently in terms of position between correction data f1 and image data f2. Therefore, effective correction can not be obtained, and irregularity is rather increased on the corrected image data f3. This is clear from the frequency spectrum shown in FIG. 24(c-2), wherein a peak of a specific frequency component is increased.

SUMMARY OF THE INVENTION

The invention has been achieved in view of the problems mentioned above, and its object is to provide a radiographic image information reading method and a radiographic image information reading apparatus which are capable of effectively eliminating the irregularity with no position repeatability from correction data.

The first invention solving the aforementioned problems is characterized to comprise the first step to cause exciting light to illuminate a radiographic image conversion panel irradiated with radiations without arranging a subject in advance, and to read photoelectrically accelerating radiation emitted from the radiographic image conversion panel to obtain the first image information, the second step to take prescribed spatial frequency processing reducing spatial frequency components on the obtained first image information or on one wherein a prescribed processing has been given to the first image information, to obtain correction data, the third step to cause exciting light to illuminate a radiographic image conversion panel irradiated with radiations with arranging a subject in advance, and to read photoelectrically accelerating radiation emitted from the radiographic image conversion panel to obtain the second image information and the fourth step to correct a signal value of each pixel based on the aforesaid correction data for the second image information to obtain image information.

In this case, the prescribed processing to be given to the first image means a processing in the intermediate stage in the case of preparing correction data from the first image information, including, for example, the first image information subjected to logarithmic conversion or linear conversion, those (difference or sum) obtained based on a prescribed standard values and the first image data, those obtained by multiplying the first image information by a prescribed number or a combination of the foregoing.

In the first invention, since the spatial frequency processing reducing prescribed spatial frequency component is given to the first image or to the first image subjected to prescribed processing, it is possible to eliminate effectively the irregularity with no position repeatability from correction data.

The second invention solving the aforementioned problems is characterized to comprise the first step to cause exciting light to illuminate a radiographic image conversion panel irradiated with radiations without arranging a subject in advance, and to read photoelectrically accelerating radiation emitted from the radiographic image conversion panel to obtain the first image information, the second step to extract one-dimensional irregularity information for at least one direction of main- and sub-scanning directions for the aforesaid first image information and to prepare the first one-dimensional correction data equivalent to at least one list based on one-dimensional irregularity information in the aforesaid direction, the third step to perform spatial frequency processing for reducing a prescribed component of spatial frequency on at least one list of the aforesaid first one-dimensional correction data and to obtain the second one-dimensional correction data, the fourth step to cause exciting light to illuminate a radiographic image conversion panel irradiated with radiations with arranging a subject in advance, and to read photoelectrically accelerating radiation emitted from the radiographic image conversion panel to obtain the second image information, and the fifth step to correct a signal value of each pixel based on the aforesaid second one-dimensional correction data for the aforesaid second image information to obtain image information.

In this case, data of one list means data of one line or of one row.

In the second invention, it is possible to eliminate effectively the irregularity with no position repeatability from correction data by extracting, from the first image information, one-dimensional irregularity information for at least one direction out of the main- and sub-scanning directions and thereby obtaining the first correction data equivalent to at least one list, and by obtaining the second one-dimensional correction data by performing, on this first correction data, the spatial frequency processing that reduces prescribed spatial frequency component.

The third invention solving the aforementioned problems is characterized to comprise the first step to cause exciting light to illuminate a radiographic image conversion panel irradiated with radiations without arranging a subject in advance, and to read photoelectrically accelerating radiation emitted from the radiographic image conversion panel to obtain the first image information, the second step to obtain the second image information by performing spatial frequency processing that reduces prescribed spatial frequency component for at least one direction out of the main- and sub-scanning directions of the aforesaid first image information, the third step to extract one-dimensional irregularity information for at least one direction out of main- and sub-scanning directions for the aforesaid second image information and to prepare the first one-dimensional correction data equivalent to at least one list based on one-dimensional irregularity information in the aforesaid direction, the fourth step to cause exciting light to illuminate a radiographic image conversion panel irradiated with radiations with arranging a subject in advance, and to read photoelectrically accelerating radiation emitted from the radiographic image conversion panel to obtain the third image information, and the fifth step to correct a signal value of each pixel based on the aforesaid one-dimensional correction data for the aforesaid third image information and thereby to obtain image information.

In the third invention, it is possible to eliminate effectively the irregularity with no position repeatability from correction data by obtaining the second image information by performing the spatial frequency processing that reduces prescribed spatial frequency component for at least one direction out of the main- and sub-scanning directions of the first image information and by extracting one-dimensional irregularity information for at least one direction out of the main- and sub-scanning directions for the second image information to prepare one-dimensional correction data equivalent to at least one list based on one-dimensional irregularity information in the aforesaid direction.

In the second invention, one-dimensional irregularity information is extracted for the main-scanning direction and the sub-scanning direction for the aforesaid first image information, then, the first one-dimensional correction data are prepared based on one-dimensional irregularity information in the aforesaid main-scanning direction and sub-scanning direction, and different spatial frequency processings are performed for the one-dimensional correction data in the main-scanning direction and that in the sub-scanning direction respectively. Due to this, it is possible to eliminate effectively the respective irregularity with no position repeatability in the main-scanning direction and that in the sub-scanning direction from the correction data.

Further, in the first invention mentioned above, different spatial frequency processings are performed respectively in the main-scanning direction and the sub-scanning direction for the first image information or one wherein a prescribed processing is performed on the first image information. Due to this, it is possible to eliminate effectively the irregularity with no position repeatability from the correction data in accordance with the scanning direction.

Further, in the third invention mentioned above, different spatial frequency processings are performed respectively in the main-scanning direction and the sub-scanning direction for the first image information. Due to this, it is possible to eliminate effectively the irregularity with no position repeatability from the correction data in accordance with the scanning direction.

The aforesaid spatial frequency processing is characterized to be low-pass filtering processing. Due to this, it is possible to eliminate effectively from the correction data when the irregularity with no position repeatability is of high-frequency components.

Further, the aforesaid spatial frequency processing is characterized to be band-cut filtering processing. Due to this, it is possible to eliminate effectively from the correction data when the irregularity with no position repeatability contains specific-frequency components.

Further, the aforesaid spatial frequency processing is characterized to be simple average processing in the direction. of a data list. Due to this, it is possible to eliminate effectively the irregularity with no position repeatability from the correction data within a short operation time.

The list of data in this case means data standing in line one-dimensionally in the main-scanning direction or in the sub-scanning direction.

It is further characterized that the aforesaid spatial frequency processing is the processing of weighted average in the direction of a data list, be simple average processing in the direction. of a data list, Due to this, it is possible to eliminate selectively the irregularity with no position repeatability alone from the correction data.

It is further characterized that cut-off frequency in the aforesaid low-pass filtering processing is 0.5–2.0 cycles/mm. Due to this, it is possible to eliminate effectively the irregularity with no position repeatability caused especially by irregularity in an inclination angle of a polygon mirror and irregularity of reflection factor in mirror surfaces from the correction data.

It is further characterized in the first invention that the aforesaid first image information is obtained in accordance with plural sampling pitches, correction data are obtained by performing spatial frequency processing on the plural first image information or on one wherein prescribed processing is given to the first image information, and the correction data used for correction are selected in accordance with a sampling pitch in the case of obtaining the aforesaid second image information.

Due to this, it is possible to eliminate effectively the irregularity with no position repeatability from the correction data.

It is further characterized in the second invention that the aforesaid first image information is obtained in accordance with plural sampling pitches, a list of the aforesaid first one-dimensional correction data based on each of the plural first image information is prepared, a list of the second one-dimensional correction data corresponding to the list of the first one-dimensional correction data is prepared, and the list of the second one-dimensional correction data used for correction is selected in accordance with sampling pitches in the case of obtaining the aforesaid third image information.

Due to this, it is possible to eliminate effectively the irregularity with no position repeatability from the correction data.

It is further characterized in the third invention that the aforesaid first image information is obtained in accordance with plural sampling pitches, the aforesaid second image information based on each of the plural first image information is prepared, a list of the aforesaid one-dimensional correction data corresponding to the second image information is prepared, and the list of the one-dimensional correction data used for correction is selected in accordance with sampling pitches in the case of obtaining the aforesaid third image information.

Due to this, it is possible to eliminate effectively the irregularity with no position repeatability from the correction data.

Further, in the first and second inventions, it is characterized that different spatial frequency processings are performed in accordance with a sampling pitch of the first image information and/or a sampling pitch of the second image information. Due to this, it is possible to eliminate effectively the irregularity with no position repeatability from the correction data in accordance with sampling pitches.

Further, in the third inventions, it is characterized that different spatial frequency processings are performed in accordance with a sampling pitch of the first image information and/or a sampling pitch of the third image information. Due to this, it is possible to eliminate effectively the irregularity with no position repeatability from the correction data in accordance with sampling pitches.

The fourth invention solving the aforementioned problems is represented by a radiographic image information reading apparatus that reads images recorded on a radiographic image conversion panel and conducts prescribed image processing wherein there are provided a first image reading means to cause exciting light to illuminate a radiographic image conversion panel irradiated with radiations without arranging a subject in advance, and to read photoelectrically accelerating radiation emitted from the radiographic image conversion panel to obtain the first image information, a first correction operation means for obtaining correction data by performing prescribed spatial frequency processing for the obtained first image information or for one wherein prescribed processing is given to the first image information, a second image reading means to cause exciting light to illuminate a radiographic image conversion panel irradiated with radiations with arranging a subject in advance, and to read photoelectrically accelerating radiation emitted from the radiographic image conversion panel to obtain the second image information and a second correction operating means for obtaining image information by correcting a signal value of each pixel based on the aforesaid correction data for the second image information.

Since the first correction operating means performs the spatial frequency processing that reduces prescribed spatial frequency component for the first image or for one wherein prescribed processing is given to the first image in the fourth invention, it is possible to eliminate effectively the irregularity with no position repeatability from the correction data.

The fifth invention solving the aforementioned problems is represented by a radiographic image information reading apparatus that reads images recorded on a radiographic image conversion panel and conducts prescribed image processing wherein there are provided a first image reading means to cause exciting light to illuminate a radiographic image conversion panel irradiated with radiations without arranging a subject in advance, and to read photoelectrically accelerating radiation emitted from the radiographic image conversion panel to obtain the first image information, a first correction operating means to extract one-dimensional irregularity information for at least one direction out of main- and sub-scanning directions for the aforesaid first image information and to prepare the first one-dimensional correction data equivalent to at least one list based on one-dimensional irregularity information in the aforesaid direction, a second correction operating means for preparing the second one-dimensional correction data by performing spatial frequency processing that reduces prescribed spatial frequency components for at least one list of the first one-dimensional correction data, a second image reading means to cause exciting light to illuminate a radiographic image conversion panel irradiated with radiations with arranging a subject in advance, and to read photoelectrically accelerating radiation emitted from the radiographic image conversion panel to obtain the second image information, and a third correction operating means for obtaining image information by correcting a signal value of each pixel based on the second one-dimensional correction data for the aforesaid second image information.

In the fifth invention wherein the first correction operating means extracts one-dimensional irregularity information for at least one direction out of the main- and sub-scanning directions from the first image information and thereby the first correction data equivalent to at least one list are obtained, and the second correction operating means performs spatial frequency processing that reduces prescribed spatial frequency components for the first correction data and thereby the second one-dimensional correction data are obtained, it is possible to eliminate effectively the irregularity with no position repeatability from the correction data.

The sixth invention solving the aforementioned problems is represented by a radiographic image information reading apparatus that reads images recorded on a radiographic image conversion panel and conducts prescribed image processing wherein there are provided a first image reading means to cause exciting light to illuminate a radiographic image conversion panel irradiated with radiations without arranging a subject in advance, and to read photoelectrically accelerating radiation emitted from the radiographic image conversion panel to obtain the first image information, a first correction operating means for obtaining image information by performing spatial frequency processing that reduces prescribed spatial frequency components for at least one direction out of the main- and sub-scanning directions of the aforesaid first image information, a second correction operating means that extracts one-dimensional irregularity information for at least one direction out of the main- and sub-scanning directions for the aforesaid second image information and thereby prepares one-dimensional correction data equivalent to at least one list based on one-dimensional irregularity information in the direction, a second image reading means to cause exciting light to illuminate a radiographic image conversion panel irradiated with radiations with arranging a subject in advance, and to read photoelectrically accelerating radiation emitted from the radiographic image conversion panel to obtain the third image information, and a third correction operating means that corrects a signal value of each pixel based on the one-dimensional correction data for the aforesaid third image information.

In the sixth invention wherein the first correction operating means performs spatial frequency processing that reduces prescribed spatial frequency components for at least one direction out of the main- and sub-scanning directions for the first image information to obtain the second image information and it extracts one-dimensional irregularity information for at least one direction out of the main- and sub-scanning directions for the second image information and thereby one-dimensional correction data equivalent to at least one list are prepared based on one-dimensional irregularity information in the direction, it is possible to eliminate effectively the irregularity with no position repeatability from the correction data.

It is characterized in the fifth invention that the aforesaid first correction operating means extracts one-dimensional irregularity information for the main- and sub-scanning directions for the aforesaid first image information, then it prepares the first one-dimensional correction data based on one-dimensional irregularity information in the main- and sub-scanning directions, and the aforesaid second correction operating means performs different spatial frequency processings for the first one-dimensional correction data in these main- and sub-scanning directions. Due to this, it is possible to eliminate effectively the irregularity with no position repeatability from the correction data.

It is characterized in the fourth invention that the aforesaid first correction operating means performs spatial frequency processing which varies between the main-scanning direction and the sub-scanning direction for the aforesaid first image information or for one wherein prescribed processing has been conducted on the first image information. Due to this, data in these main- and sub-scanning directions. Due to this, it is possible to eliminate effectively the irregularity with no position repeatability from the correction data in accordance with the scanning direction.

It is further characterized in the sixth invention that the aforesaid first correction operating means performs spatial frequency processing which varies between the main-scanning direction and the sub-scanning direction for the aforesaid first image information. Due to this, data in these main- and sub-scanning directions. Due to this, it is possible to eliminate effectively the irregularity with no position repeatability from the correction data in accordance with the scanning direction.

The aforesaid spatial frequency processing is characterized to be low-pass filtering processing. Due to this, it is possible to eliminate effectively from the correction data when the irregularity with no position repeatability is of high-frequency components.

Further, the aforesaid spatial frequency processing is characterized to be band-cut filtering processing. Due to this, it is possible to eliminate effectively from the correction data when the irregularity with no position repeatability contains specific-frequency components.

Further, the aforesaid spatial frequency processing is characterized to be simple average processing in the direction. of a data list. Due to this, it is possible to eliminate effectively the irregularity with no position repeatability from the correction data within a short operation time.

It is further characterized that the aforesaid spatial frequency processing is the processing of weighted average in the direction of a data list be simple average processing in the direction. of a data list. Due to this, it is possible to eliminate selectively the irregularity with no position repeatability alone from the correction data.

It is further characterized that cut-off frequency in the aforesaid low-pass filtering processing is 0.5–2.0 cycles/mm. Due to this, it is possible to eliminate effectively the irregularity with no position repeatability caused especially by irregularity in an inclination angle of a polygon mirror and irregularity of reflection factor in mirror surfaces from the correction data.

It is further characterized in the fourth invention that the aforesaid first image information reading means obtains the aforesaid first image information for plural sampling pitches, the aforesaid first correction operating means prepares a list of correction data corresponding to each of the plural pieces of first image information and the aforesaid second correction operating means selects a list of the correction data used for correction in accordance with sampling pitches in the case of obtaining the second image information. Due to this, it is possible to eliminate effectively the irregularity with no position repeatability from the correction data in accordance with sampling pitches.

It is further characterized in the fifth invention that the aforesaid first image information reading means obtains the aforesaid first image information for plural sampling pitches, the aforesaid first correction operating means prepares a list of the first one-dimensional correction data corresponding to each of the plural pieces of first image information, the aforesaid second correction operating means prepares a list of the second one-dimensional correction data corresponding to the list of the first one-dimensional correction data, and the aforesaid third correction operating means selects the list of the second one-dimensional correction data used for correction in accordance with sampling pitches in the case of obtaining the second image information. Due to this, it is possible to eliminate effectively the irregularity with no position repeatability from the correction data in accordance with sampling pitches.

It is further characterized in the sixth invention that the aforesaid first image information reading means obtains the aforesaid first image information for plural sampling pitches, the aforesaid first correction operating means prepares the second image information corresponding to each of plural pieces of first image information, the aforesaid second correction operating means prepares a list of one-dimensional correction data based on the second image information, and the aforesaid third correction operating means selects the list of the second one-dimensional correction data used for correction in accordance with sampling pitches in the case of obtaining the second image information. Due to this, it is possible to select the list of the optimum correction data according to sampling pitches, and to eliminate effectively the irregularity with no position repeatability from the correction data.

It is further characterized that different spatial frequency processing is given depending on the sampling pitch of the aforesaid first image information and/or the sampling pitch of the aforesaid second image information. Due to this, it is possible to eliminate effectively the irregularity with no position repeatability from the correction data.

It is further characterized that different spatial frequency processing is given depending on the sampling pitch of the aforesaid first image information and/or the sampling pitch of the aforesaid third image information. Due to this, it is possible to eliminate effectively the irregularity with no position repeatability from the correction data.

BRIEF DESCRIPTION OF THE DRAWINGS

FIGS. 6(a) and 6(b) represent illustrations each showing operations of an example of frequency processing of the invention.

FIGS. 12(a) through 12(d) represent illustrations each showing operations of an example wherein different frequency processing is performed depending on a sampling pitch of image information of the invention.

FIGS. 24(a-1) through 24(c-2) represent illustrations of problems of conventional technologies.

FIGS. 25(a-1) through 25(d-2) represent illustrations of operations of the invention.

DETAILED DESCRIPTION OF THE PREFERRED EMBODIMENT

Figure 1:
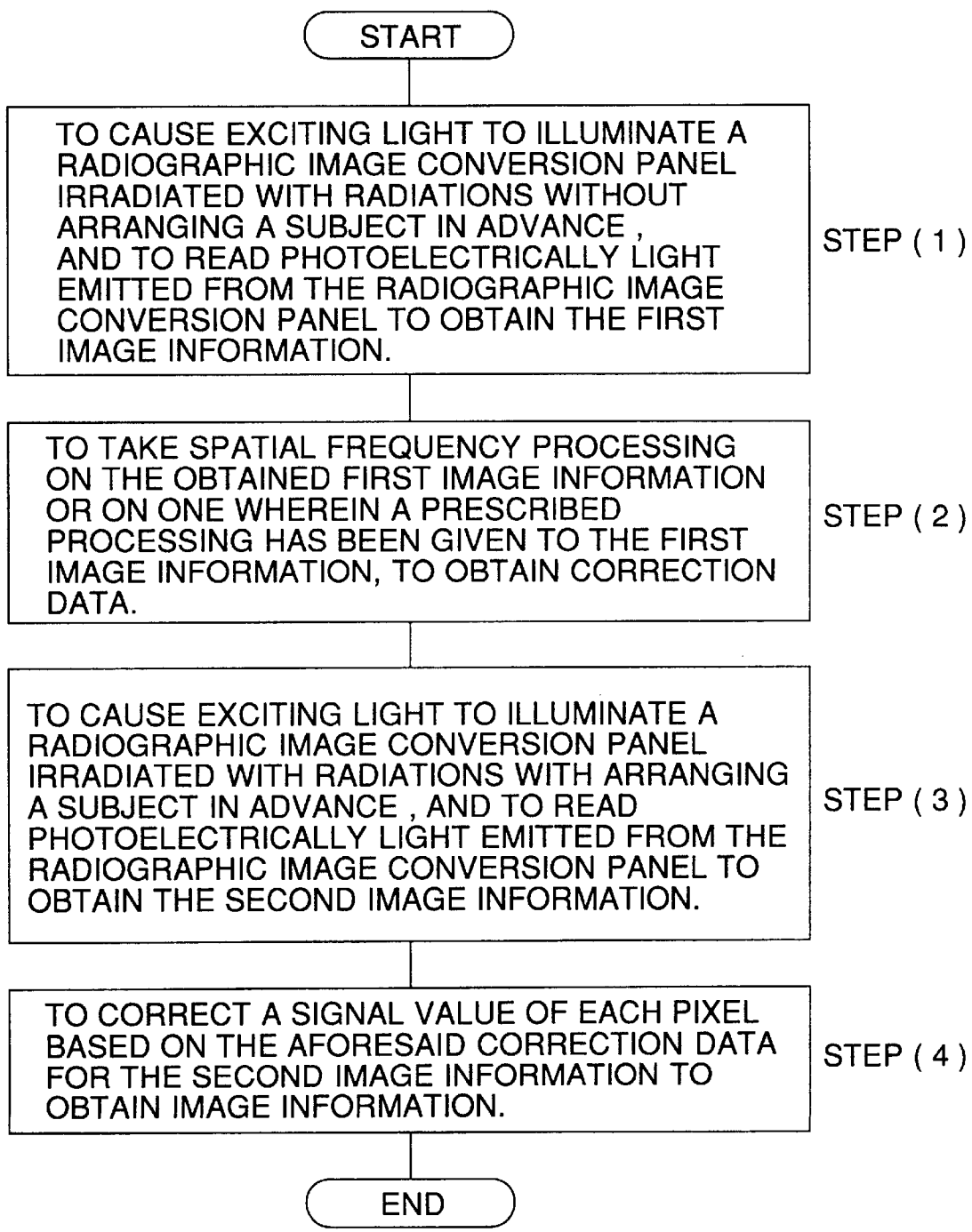
FIG. 1 is a flowchart showing a principle of a method of the invention.

Embodiments of the invention will be explained in detail as follows, referring to the drawings.

FIG. 1 is a flowchart showing the principles of a method of the invention. A basis of the method of the invention is, as shown in the illustration, to cause exciting light to illuminate a radiographic image conversion panel irradiated with radiations without arranging a subject in advance, and to read photoelectrically accelerating radiation emitted from the radiographic image conversion panel and thereby to obtain the first image information (Step (1)), to perform prescribed spatial frequency processing reducing spatial frequency components on the obtained first image information or on one wherein a prescribed processing has been given to the first image information (Step (2)), to obtain second image information by causing exciting light to illuminate a radiographic image conversion panel irradiated with radiations with arranging a subject in advance (Step (3)), and to obtain image information by correcting a signal value of each pixel based on the aforesaid correction data for the second image information (Step (4)).

It is generally normal that frequency components corresponding to the streak-shaped irregularity with no position repeatability or the irregularity having no positional relation with an image as those described above are limited within a certain range. Under that condition, a certain spatial frequency processing is performed on an image obtained without any subject so that frequency components in a certain range may be reduced. By using such method, it is possible to eliminate the irregularity with no position repeatability from correction data and thereby to obtain accurate information.

FIGS. 25(a-1) to 25(d-2) represent illustrations of operations of the invention. In the figure, f1 in FIG. 25(a-1) represents correction data before processing, FIG. 25(a-2) represents a frequency spectrum of f1, the symbol f2 in FIG. 25(b-1) represents correction data after processing, FIG. 25(b-2) represents a frequency spectrum of f2, the symbol f3 in FIG. 25(c-1) represents image data before correction, and FIG. 25(c-2) represents a frequency spectrum of f3. The symbol f4 in FIG. 25(d-1) represents image data after correction, and FIG. 25(d-2) represents a frequency spectrum of f4. The axes of ordinate for f1–f4 represent a size of image data, and the axes of abscissa represent positions, while the axis of ordinate of frequency spectrum represents intensity and the axis of abscissa represents spatial frequency. As shown in FIG. 25(a-1), when irregularity with no position repeatability is caused on correction data, correction data shown in FIG. 25(b-1) can be obtained by reducing frequency components within a certain range, and when this obtained correction data are used for correcting image data in FIG. 25(c-1), image data in FIG. 25(d-1) after correction can be obtained without irregularity increased by the correction.

Figure 26:
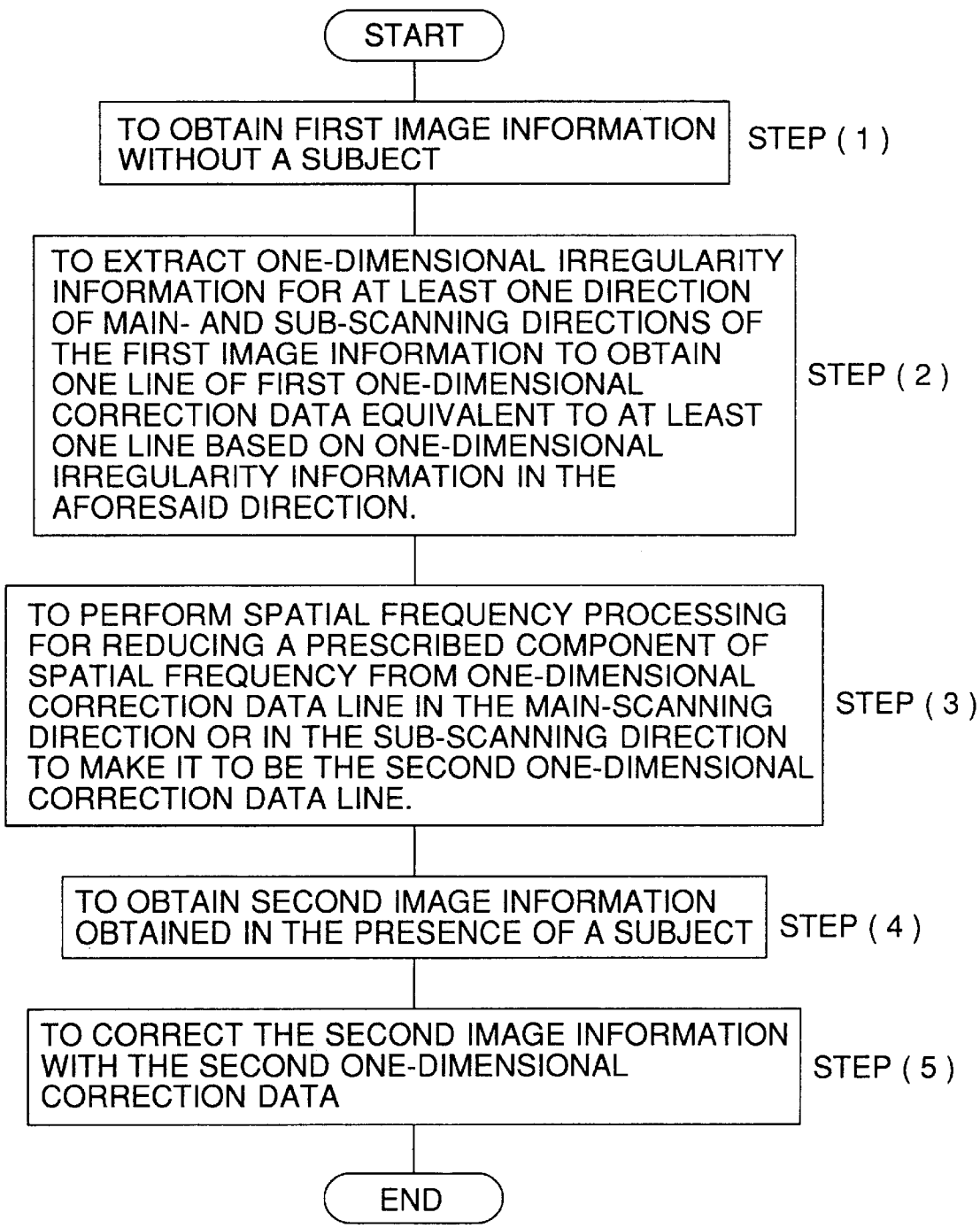
FIG. 26 is a flowchart showing an example of a method of the invention.

Owing to a radiographic image information reading method shown in FIG. 1, it is possible to realize an extremely excellent image information reading method capable of conducting correcting in the main-scanning direction and/or sub-scanning direction by using correction data from which the irregularity with no position repeatability has been eliminated. FIG. 26 is a flowchart showing an example of a method of the invention. For example, the first image information obtained with no subject is obtained (Step (1)), then one-dimensional irregularity information is extracted for at least one direction out of the main-scanning direction or the sub-scanning direction of the first image information, and a list of the first one-dimensional correction data equivalent of at least one list is obtained based on the one-dimensional irregularity information in the aforesaid direction and on the prescribed standard value (Step (2). see FIG. 21). In the aforesaid manner, a prescribed spatial frequency processing reducing spatial frequency components is performed for a list of one-dimensional correction data in the main-scanning direction and/or the sub-scanning direction, which is made to be a list of the second one-dimensional correction data (Step (3)). Then, when the second image information is corrected by the list of the second one-dimensional correction data (Step (5)) by obtaining the second image information obtained under existence of a subject (Step (4)), it is possible to conduct the correction in the main-scanning direction and/or the sub-scanning direction by using the correction data from which irregularity with no position repeatability has been eliminated. Thus, it is possible to obtain extremely accurate image information.

Figure 27:
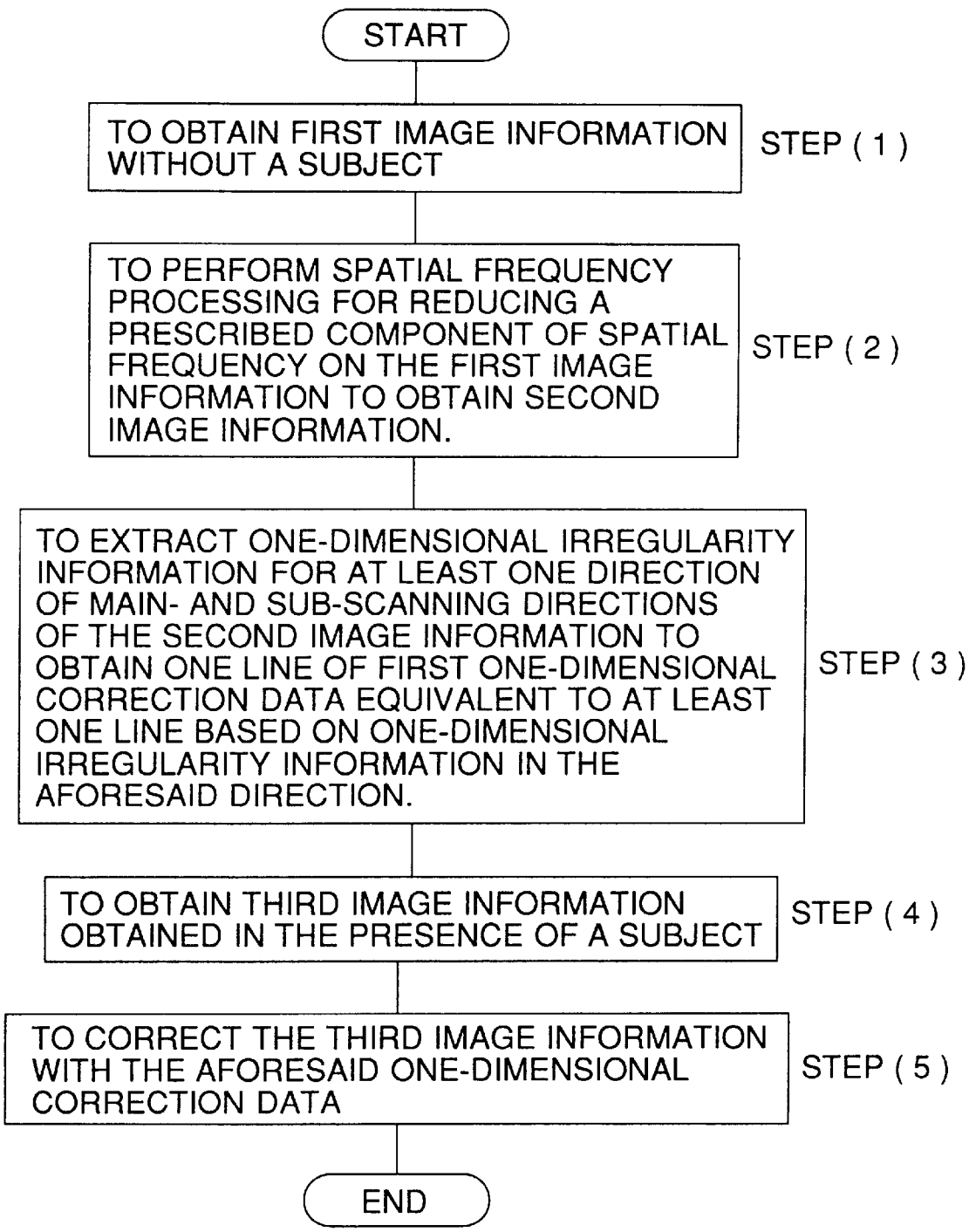
FIG. 27 is a flowchart showing another example of a method of the invention.

In the example explained above, a list of one-dimensional correction data is prepared from the first image information obtained under existence of no subject, and spatial frequency processing is performed for the list of the one-dimensional correction data. However, the invention is not limited thereto, and it is also possible to perform spatial frequency processing for the first image information obtained under existence of no subject and thereby to obtain the list of one-dimensional correction data for the second image information obtained through the foregoing. FIG. 27 is a flowchart showing another example of the invention. Namely, the first image information obtained under existence of no subject is obtained (Step (1)), then prescribed spatial frequency processing reducing spatial frequency components is performed for the first image information to obtain the second image information (Step (2)), then one-dimensional irregularity information is extracted for at least one direction out of the main-scanning direction or the sub-scanning direction of the second image information to obtain a list of one-dimensional correction data equivalent to at least one list based on the one-dimensional irregularity information in the aforesaid direction (Step (3)), then the third image information obtained under existence of a subject is obtained (Step (4)), and the third image information is corrected by the aforesaid one-dimensional correction data (Step (5)).

Even in the aforesaid method, it is also possible to conduct correction in the main-scanning direction and/or sub-scanning direction by using the correction data from which the irregularity with no position repeatability. Therefore, it is possible to obtain extremely accurate image information. However, it requires less operation time and is more advantageous to obtain a list of one-dimensional correction data first and then to perform frequency processing for the list, because of less amount of data.

Further, with regard to the aforesaid list of correction data, it is not necessary to have one list for each of the main-scanning direction and the sub-scanning direction, but it is also possible to have plural lists. In this case, it is preferable that these plural lists of correction data are used properly depending on image areas.

Figure 2:
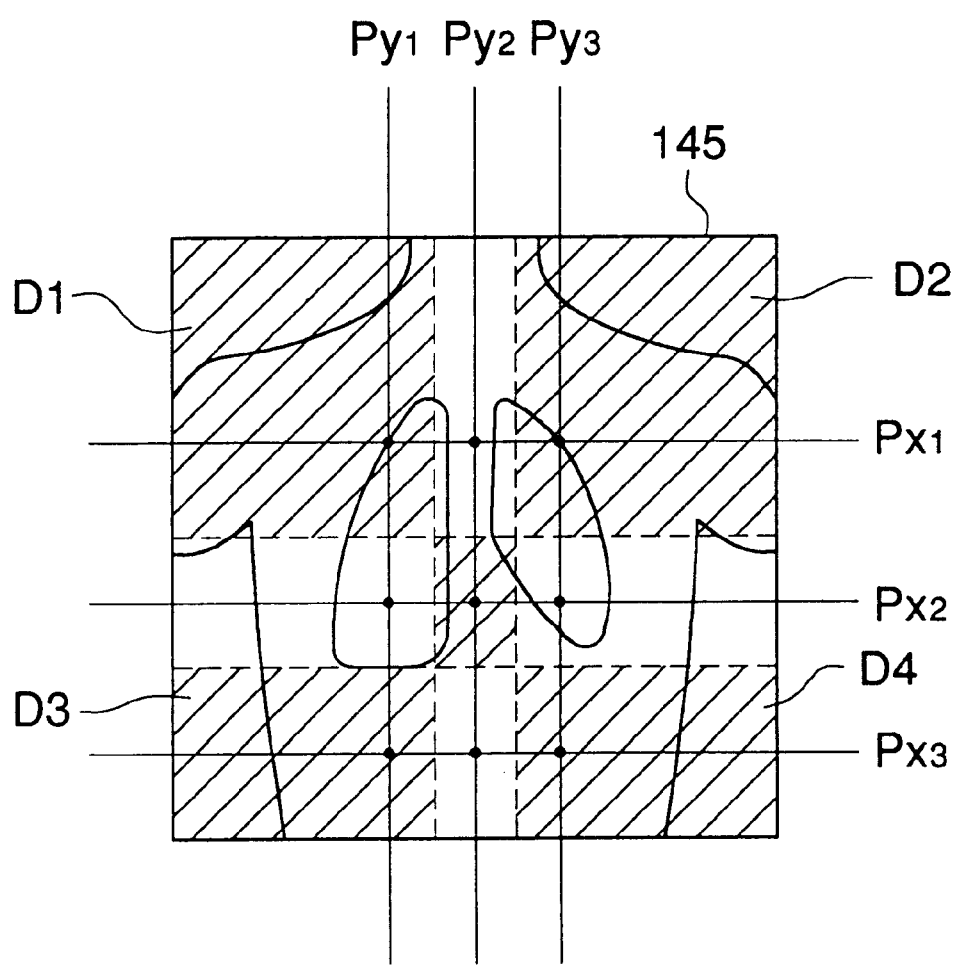
FIG. 2 is a diagram showing an example having a plurality of lists of correction data.

FIG. 2 is a diagram showing an example to have plural lists in the main-scanning direction and in the sub-scanning direction respectively. In the figure, the numeral 145 represents image information under existence of a subject, and Px1, Px2 and Px3 represent respectively a list of one-dimensional correction data in the main-scanning direction, Py1, Py2 and Py3 represent respectively a list of one-dimensional correction data in the sub-scanning direction. In this way, each of the main-scanning direction and the sub-scanning direction has plural lists of one-dimensional correction data, and the lists of correction data are used properly depending on image areas. For example, a list of correction data (Px1, Py1) is used for area D1, while, a list of correction data (Px1, Py3) is used for area D2. In this way, optimum correction can be conducted depending on areas.

In this case, it is not always necessary to use all one-dimensional correction data for the spatial frequency processing, but it may also be possible to use a part of correction data for the spatial frequency processing. For example, when an area where irregularity with no position repeatability takes place is known to a certain extent (for example, area D1 in the above-mentioned example), spatial frequency processing has only to be performed for a part of correction data (Px1, Py1) corresponding to the area.

Next, examples of the invention will be explained in detail as follows. A streak-shaped irregularity with no position repeatability appears differently between the main-scanning direction and the sub-scanning direction, and it appears more in the sub-scanning direction. Therefore, when performing prescribed spatial frequency processing reducing spatial frequency components for a list of one-dimensional correction data in the aforesaid main-scanning direction and for a list of one-dimensional correction data in the sub-scanning direction, it is preferable to perform different spatial frequency processing for the list of one-dimensional correction data in the aforesaid main-scanning direction and for the list of one-dimensional correction data in the sub-scanning direction respectively. The different spatial frequency processing, in this case, means that a degree of reduction of spatial frequency components and a frequency zone to be reduced are changed depending on the direction. In particular, it is preferable to make the degree of reduction in the sub-scanning direction to be great or to make the frequency zone reduced in the sub-scanning direction to be broad. Due to this, it is possible to eliminate surely the irregularity with no position repeatability of correction data in the main-scanning direction and/or the sub-scanning direction.

Further, spatial frequency components corresponding to a streak-shaped irregularity with no position repeatability have, in many cases, a sharp peak in a relatively high frequency band or in a medium frequency band. Therefore, it is preferable to conduct the processing wherein components of a low frequency band remain untouched and specific frequency components in medium—high frequency bands are reduced selectively down to 10% or lower, and it is more preferable to reduce down to 1% or lower. As a method like this, there is given a low-pass filtering processing or a band-cut filtering processing.

Figure 3:
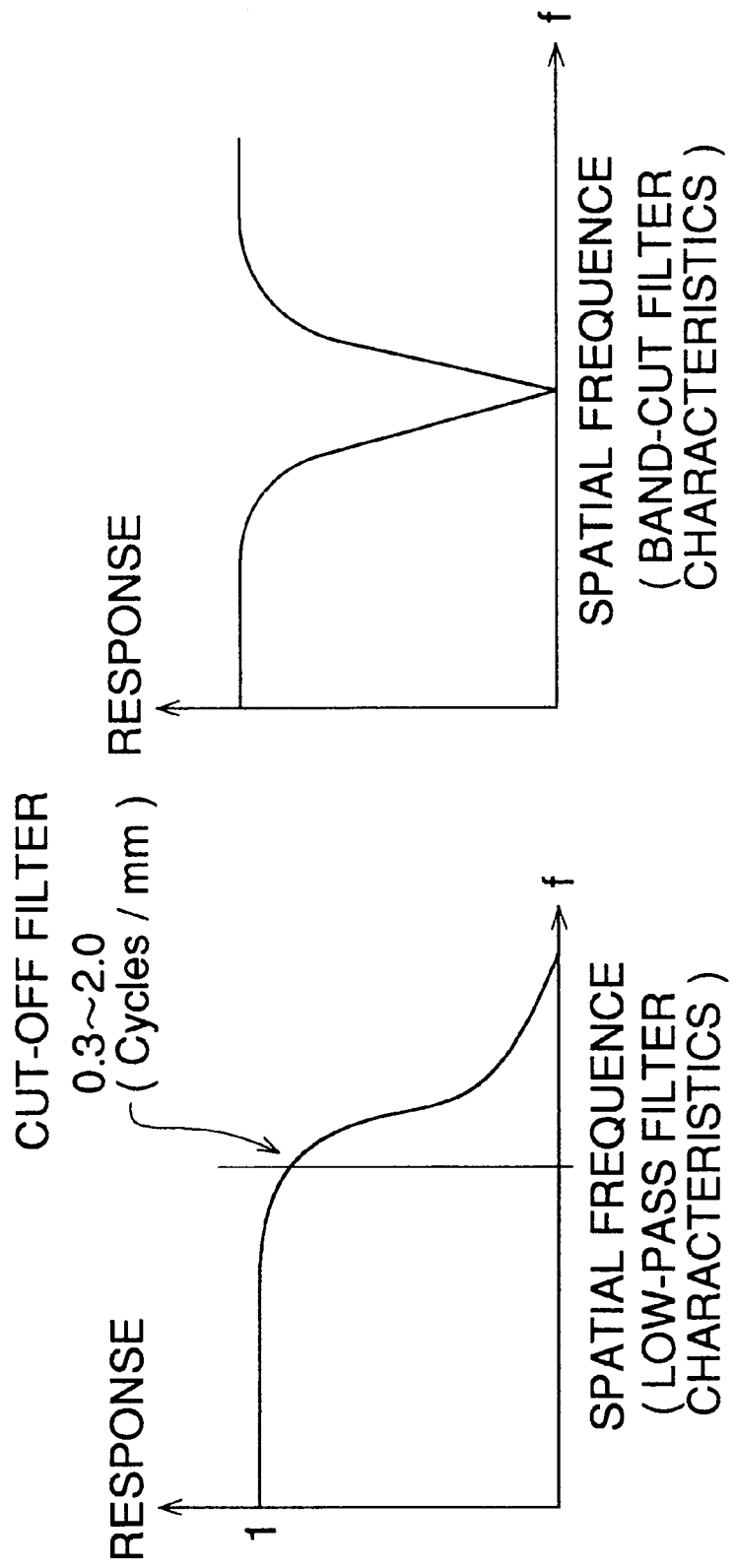
FIGS. 3(a) and 3(b) represent diagrams showing examples of characteristics of filters used in the invention.

FIG. 3 is a diagram showing examples of characteristics of filters used in the invention. The symbol (a) represents characteristics of a low-pass filter and (b) represents characteristics of a band-cut filter. In both cases, the axis of ordinate represents responses and the axis of abscissa represents spatial frequencies. As is shown in (a), the low-pass filter makes only low frequency components to pass and cuts medium—high frequency components. The band-cut filter cuts only specific frequency bands and makes other frequency bands to pass, as shown in (b).

Figure 4:
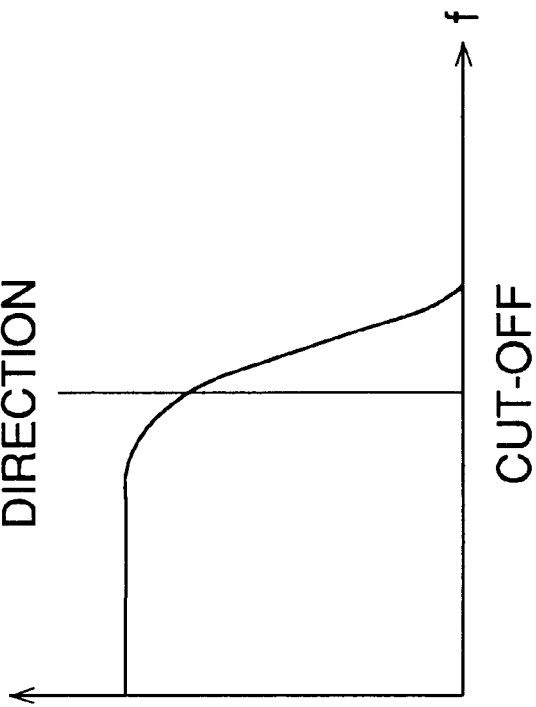
FIGS. 4(a) and 4(b) represent diagrams showing examples of characteristics of filters used respectively in the occasions wherein different frequency processing is performed for each of main-scanning direction and sub-scanning direction of the invention.
Figure 4:
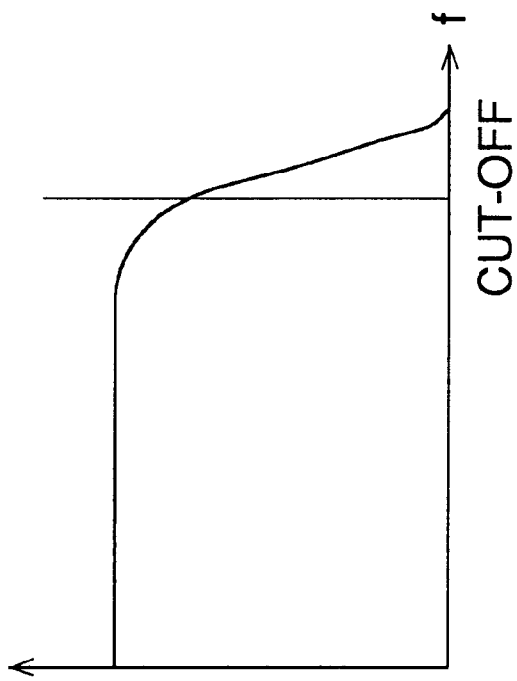

FIG. 4 is a diagram showing examples of characteristics of filters used in the occasion where different frequency processing is performed respectively in the main-scanning direction and the sub-scanning direction of the invention. In the figure, the axis of ordinate represents responses and the axis of abscissa represents spatial frequencies. The symbol (a) represents low-pass filter characteristics in the main-scanning direction, while (b) represents low-pass filter characteristics in the sub-scanning direction. As is apparent from the figure, a bandwidth in terms of frequency passing in the main-scanning direction is greater than that in the sub-scanning direction. Since the frequency band corresponding to the irregularity with no position repeatability in the sub-scanning direction are broad as stated above, a frequency band to be reduced in the sub-scanning direction is arranged to be broad. By using such low-pass filter for the lists of correction data in the main-scanning direction and the sub-scanning direction, it is possible to eliminate surely the irregularity with no position repeatability containing high frequency components respectively in the main-scanning direction and the sub-scanning direction. In the case of low-pass filtering processing, it is preferable that the cut-off frequency is 0.3–2.0 cycles/mm, and it is especially preferable that the cut-off frequency is 0.5–1.5 cycles/mm.

Figure 5:
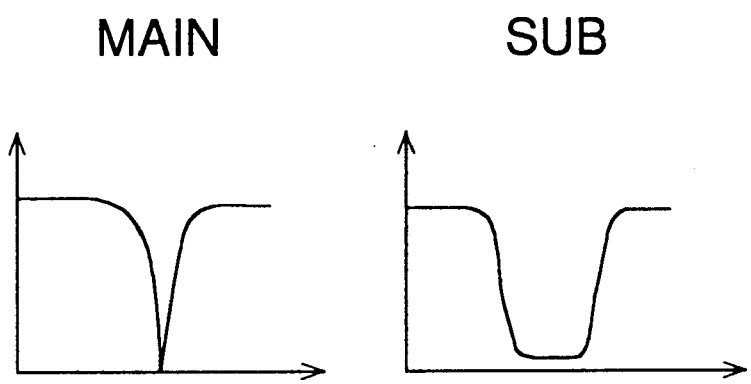
FIGS. 5(a) and 5(b) represent diagrams showing other examples of characteristics of filters used respectively in the occasions wherein different frequency processing is performed for each of main-scanning direction and sub-scanning direction of the invention.
Figure 5:
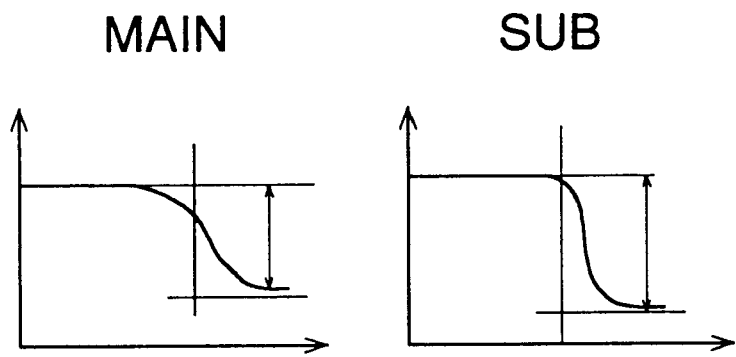

FIG. 5 is a diagram showing other examples of characteristics of filters used in the occasion where different frequency processing is performed respectively in the main-scanning direction and the sub-scanning direction of the invention. In the figure, (a) represents the occasion where a band-cut filter is used for both the main-scanning direction and the sub-scanning direction, while, (b) represents the occasion where a band-cut filter that reduces greatly only for the sub-scanning direction is used for both the main-scanning direction and the sub-scanning direction. In the case of (a), a range of band-cut is broadened because distribution of frequencies contained in irregularity with no position repeatability in the sub-scanning direction is broader than that in the main-scanning direction. the main-scanning direction and the sub-scanning direction. In the case of (b), a degree of reduction is set to be greater because signal intensity of irregularity in he sub-scanning direction is greater than that in the main-scanning direction. In this way, a list of one-dimensional correction data subjected to frequency processing can be obtained. Even in this example, it is possible to eliminate surely the irregularity with no position repeatability in each of the main-scanning direction and the sub-scanning direction.

With regard to a practical method of frequency processing, any method can be used provided that it can reduce specific spatial frequency components in a list of correction data. For example, filtering processing such as simple average or weighted average can be conducted for a list of correction data. FIG. 6 represents illustrations of operations in frequency processing examples of the invention, wherein (a) shows an example of simple average and (b) shows an example of weighted average. The example in (a) shows that correction data before frequency processing in the main-scanning direction or in the sub-scanning direction are assumed to be di-j and j is added for the point of looked pixel I and for the points preceding and succeeding the looked pixel. In (a), the axis of ordinate represents a coefficient and the axis of abscissa represents a position in the line direction or in the row direction. In this example, the quotient obtained by dividing what is added simply in the position direction with the total number (m+n+1) of data is defined to be correction data d'i after frequency processing at the point i, and d'i after processing is represented by the following formula.

$$d'i = \sum_{j=-n}^{m} \frac{1}{m+n+1} di - j \quad (1)$$

$$= \frac{1}{m+n+1} \sum_{j=-n}^{m} di - j$$

(m and n represent an integer which is not negative)

In the formula (1), a plurality of values of pixels located before and behind a pixel at the point i are added and an average thereof is obtained. For example, in the assumption that n=1 and m=1, data to be added include a value preceding the looked pixel i, the looked pixel itself and a value succeeding the looked pixel. In a word, the number of addition in this case is 3, and an average is obtained by multiplying by ⅓. An example in the figure shows that data preceding the looked pixel and data succeeding the looked pixel are added after being multiplied by ⅓. By doing such simple average processing, it is possible to obtain a list of one-dimensional correction data subjected to frequency processing for the main-scanning direction and/or the sub-scanning direction, and to eliminate irregularity with no position repeatability.

In (b), the axis of ordinate represents weighting coefficient k and the axis of abscissa represents a position in the line direction or in the row direction. In this example, the sum of those each being multiplied by a weighting coefficient in the positional direction is defined to be a pixel value at that point. Namely, in the assumption that a pixel value before processing is di and a pixel value before processing is d'i, d'I after processing is represented by the following formula.

$$d'i = \sum_{j=-n}^{m} kj \cdot di - j \quad (2)$$

In formula (2), the sum of those being data di-j before frequency processing for pixels preceding and succeeding looked pixel i each being multiplied by coefficient k is defined to be data after frequency processing at the pixel i. Incidentally, it is preferable that weighted average kj satisfies the following.

$$d'i = \sum_{j=-n}^{m} kj = 1 \quad (3)$$

With regard to pixels preceding and succeeding this weighted average, it is possible to make an arrangement so that two pixels preceding the weighted average and two pixels succeeding it are used. By performing such weighted average, it is possible to obtain a list of one-dimensional correction data wherein frequency processing has been performed in the main-scanning direction and/or sub-scanning direction, and thereby to eliminate irregularity with no position repeatability.

Figure 7C:
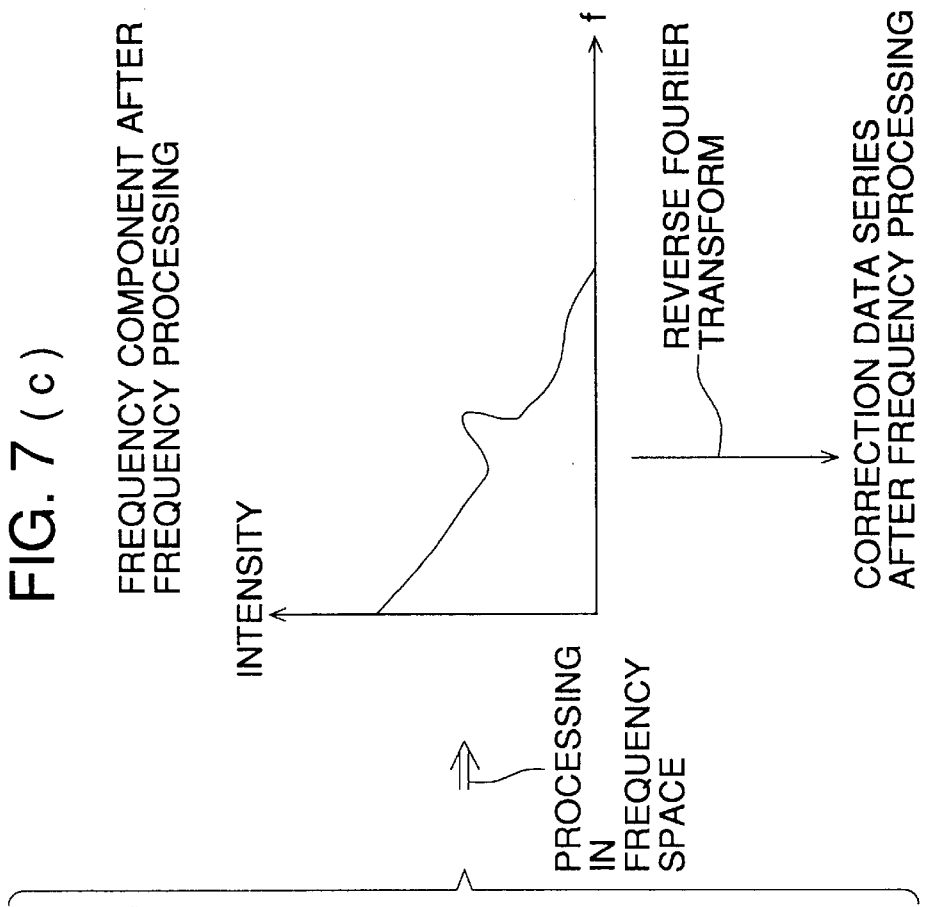
FIGS. 7(a) to 7(c) represent illustrations showing operations of another example of frequency processing of the invention.
Figure 7A:
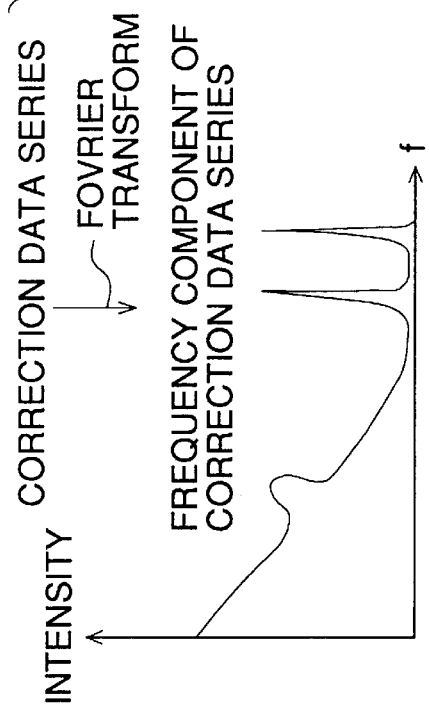
Figure 7B:

FIG. 7 represents illustrations each showing operations of another example of frequency processing of the invention. In these examples, a list of correction data is Fourier-transformed, and then is subjected to reverse Fourier transform after being multiplied by filter characteristics in a frequency space so that the list of one-dimensional correction data subjected to frequency processing may be obtained. In FIG. 7, (a) represents a diagram showing that a list of correction data is subjected to Fourier transform. The axis of abscissa represents spatial frequency, and the axis of ordinate represents intensity. This correction data may be either for the main-scanning direction or for the sub-scanning direction. In this case, there is shown an example wherein a high frequency band has therein frequency components which cause irregularity with no position repeatability. So, these frequency components are multiplied by low-pass filter characteristics shown in (b) so that so that the frequency components in the high frequency band may be cut. As a result, frequency components shown in (c) which are free from the frequency components in the high frequency band can be obtained. These characteristics shown in (c) are subjected to reverse Fourier transform so that they may return to their original pixel data. As a result, a list of correction data thus obtained does not contain high frequency components. Owing to the example mentioned above, as stated above, it is possible to obtain a list of one-dimensional correction data wherein frequency processing has been performed in the main-scanning direction and/or sub-scanning direction, and thereby irregularity with no position repeatability can be eliminated.

Incidentally, among examples shown in FIGS. 6 and 7, the weighted average processing is especially preferable because reduction characteristics can be established freely and operation is easy. With regard to a coefficient for a weighted average, it can either be obtained based on a specific function such as, for example, a SINC function, or be obtained by Fourier-transforming reversely the desired frequency characteristics. When multiplying by an appropriate window function for obtaining a coefficient based on a function, no beat is caused for the degree of reduction, which is preferable. A window function includes a Hamming window function, a Hanning window function, a Blackman window function, and variations thereof.

Figure 8:
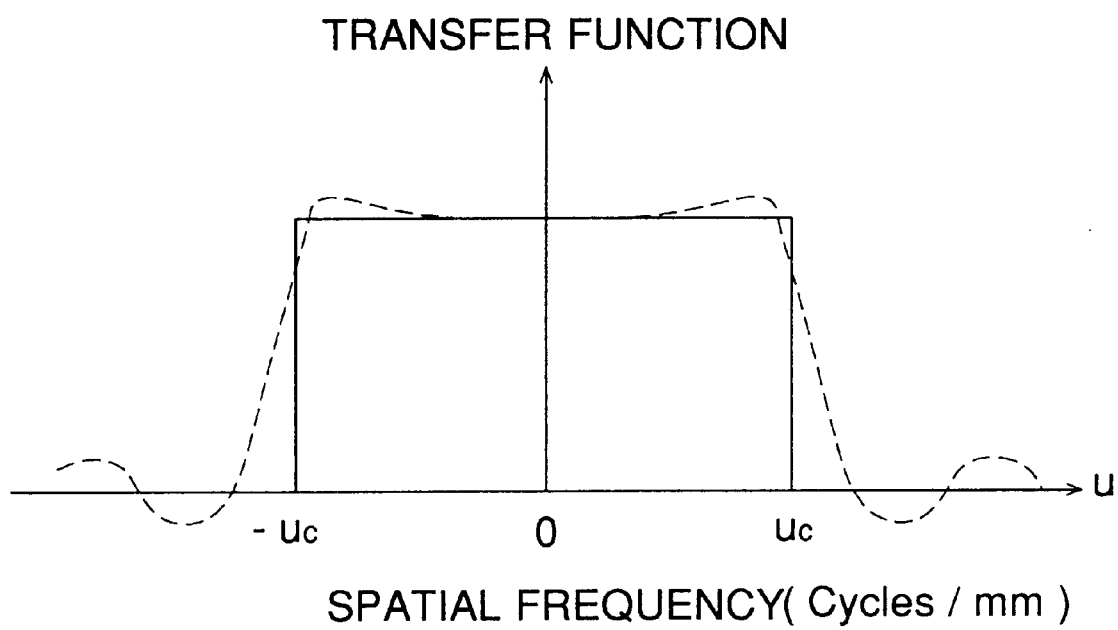
FIG. 8 is a diagram showing a transfer function.
Figure 9:
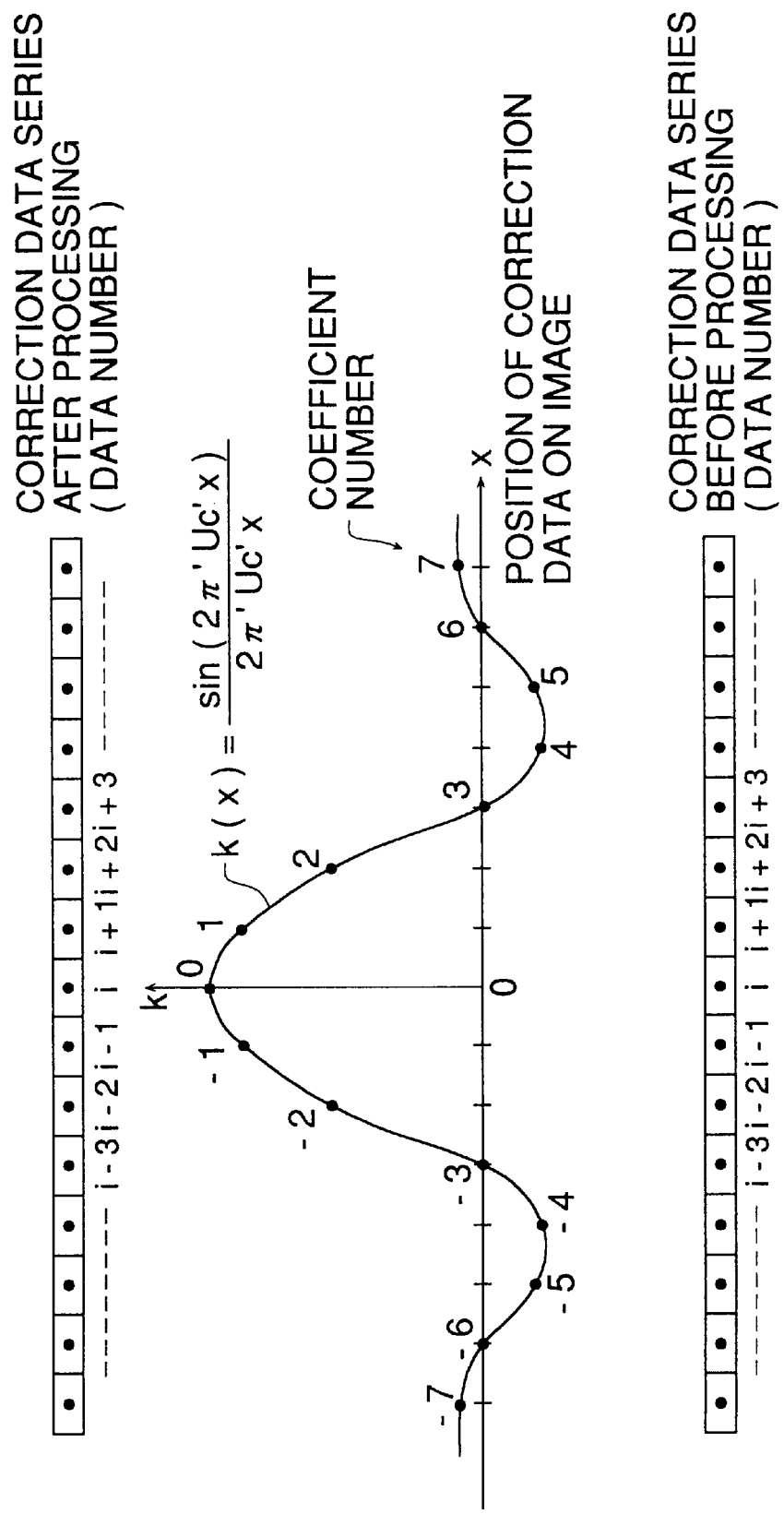
FIG. 9 is a diagram showing a waveform of coefficient k.

For example, for performing filtering processing so that a transfer function may take "1" when an absolute value of s spatial frequency is not more than Uc and take "0" when the absolute value is not less than Uc as shown in FIG. 8, coefficient k of a weighted average can be determined based on a SINC function. When the axis of abscissa represents a position on the correction data image and the axis of ordinate represents coefficient k (x) at each position as shown in FIG. 9, k(x) is represented by the following formula;

$$k(x) = \alpha \frac{\sin(2\pi \cdot Uc \cdot X)}{2\pi \cdot Uc \cdot X} \quad (4)$$

wherein, $\alpha$ is a standardized constant.

When this is applied to discrete data (coefficient number is assumed to be j) whose sampling pitch is p, $$kj = \alpha \frac{\sin(2\pi \cdot Uc \cdot p \cdot j)}{2\pi \cdot Uc \cdot X \cdot j} \quad (5)$$

holds. When assuming that di represents correction data before frequency processing and d'i represents correction data after frequency processing, d'i is represented by the following formula.

$$d'i = \sum_{j=-\infty}^{\infty} kj \cdot di - j \quad (6)$$

However, it is not practical that j is changed from $-\infty$ to $\infty$. It is therefore general that j is changed within a limited number N. Namely, $$d'i = \sum_{j=n1}^{n2} kj \cdot di - j \quad (7)$$

(n1 and n2 represent integers satisfying n1$\leq$n2) holds. For example, as an example for N which is an odd number, $$d'i = \sum_{j=-\frac{N-1}{2}}^{\frac{N-1}{2}} kj \cdot di - j \quad (8)$$

provided that $$\frac{1}{\alpha} = \sum_{j=-\frac{N-1}{2}}^{\frac{N-1}{2}} \frac{\sin(2\pi \cdot Uc \cdot p \cdot j)}{2\pi \cdot Uc \cdot p \cdot j} \quad (9)$$

hold. For N which is an even number, $$d'i = \sum_{j=-\frac{N}{2}+1}^{\frac{N}{2}} kj \cdot di - j \quad (10)$$

provided that $$\frac{1}{\alpha} = \sum_{j=-\frac{N}{2}+1}^{\frac{N}{2}} \frac{\sin(2\pi \cdot Uc \cdot p \cdot j)}{2\pi \cdot Uc \cdot p \cdot j} \quad (11)$$

or $$d'i = \sum_{j=-\frac{N}{2}}^{\frac{N}{2}-1} kj \cdot di - j \quad (12)$$

provided that $$\frac{1}{\alpha} = \sum_{j=-\frac{N}{2}}^{\frac{N}{2}-1} \frac{\sin(2\pi \cdot Uc \cdot p \cdot j)}{2\pi \cdot Uc \cdot p \cdot j} \quad (13)$$

holds.

When applying to N which is a limited number as in the foregoing, a beat sometimes takes place on the transfer function as shown by dotted lines in FIG. 8. As a method for reducing such beat, a method to multiply by a window function is known. Namely, there holds $$d'i = \sum_{j=n1}^{n2} kj \cdot Wj \cdot di - j \quad (14)$$

provided that $$\frac{1}{\alpha} = \sum_{j=n1}^{n2} kj \cdot Wj \quad (15)$$

wherein, wj represents a window function. As a window function, a Hanning window, a Hamming window, a generalized Hamming window, a Bartlett window, a Blackman window and a Kaiser window are known. For example, when applying to N which is an odd number, the following window functions are cited (in this case, $-(N-1)/2 \leq j \leq (N-1)/2$).

(1) Rectangular window $$wj = 1 \quad (16)$$

(2) Generalized window $$Wj = \alpha + (1-\alpha)\cos\left(\frac{2\pi j}{N-1}\right) \quad (17)$$

a Hanning window for $\alpha = 0.5$
a Humming window for $\alpha = 0.54$ (3) a Bartlett window $$Wj = 1 - \left|\frac{2j}{N-1}\right| \quad (18)$$

(4) a Blackman window $$Wj = 0.42 - 0.5\cos\left(\frac{2\pi j}{N-1}\right) + 0.08\cos\left(\frac{4\pi j}{N-1}\right) \quad (19)$$

(5) a Kaiser window $$W_j = \frac{Io\left[\alpha\sqrt{1-\left(1-\frac{2j}{N-1}\right)^2}\right]}{I \cdot [\alpha]} \quad (20)$$

$$4 < \alpha < 9$$

$$Io[\alpha] \simeq 1 + \sum_{l=1}^{L}\left(\frac{(\alpha/2)^l}{l!}\right)^2$$

(L is to be selected to around 15)

Io[ ] is first-class Bessel function of N-degree

When there is made an arrangement wherein image information under existence of no subject are obtained for plural sampling pitches and thereby a plurality of lists of correction data are prepared based on the image information and are stored in advance, and these lists of correction data used for correction are selected in accordance with sampling pitches used for obtaining image information under existence of a subject, an effect of eliminating streak-shaped irregularitys is high, which is preferable. In this case, it is more preferable if different frequency processing is performed depending on sampling pitches for reading image information under existence of no subject and/or sampling pitches for reading image information under existence of a subject.

In the case of an arrangement wherein plural sampling pitches can be selected when reading image information under existence of a subject, it is preferable to prepare also a list of correction data in accordance with each sampling pitch. In obtaining lists of correction data corresponding to plural sampling pitches, when reading image information under existence of no subject, reading is conducted with all sampling pitches selectable in reading of image information under existence of a subject, then lists of correction data corresponding to sampling pitches are prepared, thus it is possible to correct by using the lists of correction data corresponding to sampling pitches for reading image information under existence of a subject.

It is also possible that when reading image information under existence of no subject, a part of sampling pitches which are selectable in reading image information under existence of a subject is used for the reading, and from the image information under existence of no subject read with that part of sampling pitches, lists of correction data corresponding to all sampling pitches are prepared and stored, thus the correction data corresponding to a sampling pitch for reading image information under existence of a subject is used for the correction.

Figure 10:
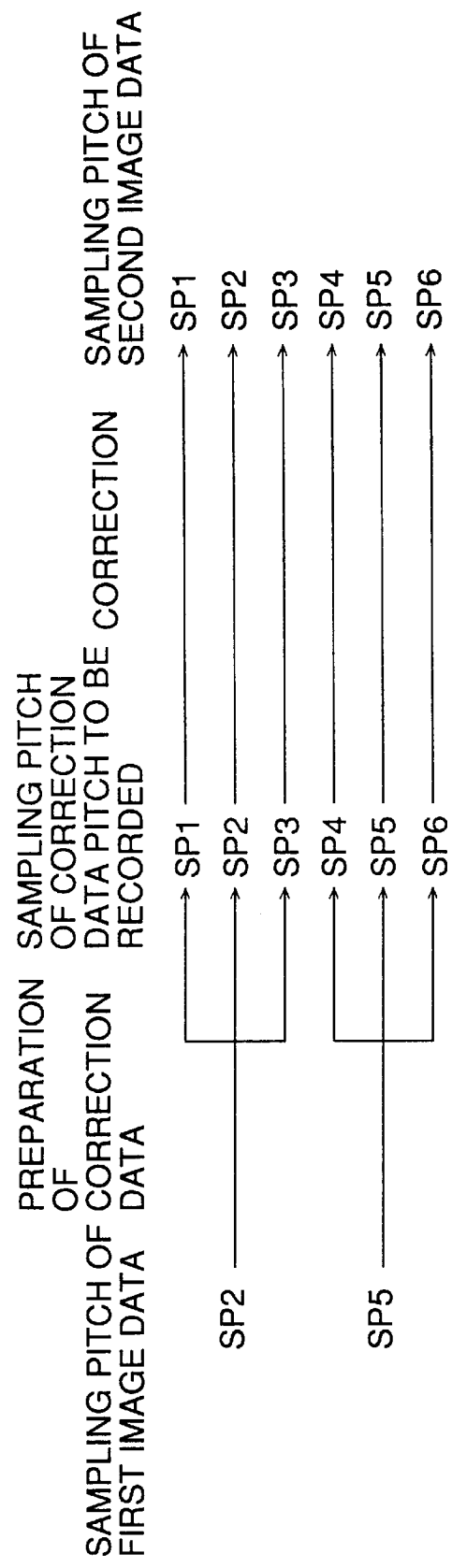
FIG. 10 is an illustration showing operations of an example wherein image information are obtained for a plurality of sampling pitches of the invention.

FIG. 10 is an illustration showing operations of an example wherein image information are obtained for a plurality of sampling pitches of the invention. Let it be assumed that sampling pitches for obtaining second image information (image information under existence of a subject) are SP1–SP6. As sampling pitches used for reading the first image information (image information under existence of no subject), some of the sampling pitches SP1–SP6, such as SP2 and SP5, for example are used. From image information obtained by the use of two sampling pitches, there are prepared six pieces of correction data. Namely, lists of correction data corresponding to SP1–SP3 are prepared from images obtained from sampling pitch SP2, and correction data corresponding to SP4–SP6 are prepared from images obtained from sampling pitch SP5. For the sampling pitch used for reading the second image, correction data in accordance with each corresponding sampling pitch are used for the correction. In the present example, it is possible to correct irregularity by the use of optimum correction data in accordance with sampling pitches.

It is also possible that when reading image information under existence of no subject, a part of sampling pitches which are selectable in reading image information under existence of a subject is used for the reading, and from the image information under existence of no subject read with that part of sampling pitches, lists of correction data corresponding to all sampling pitches are prepared and stored, thus, the correction is made while obtaining correction data of corresponding sampling pitches by the use of the stored correction data.

Figure 11:
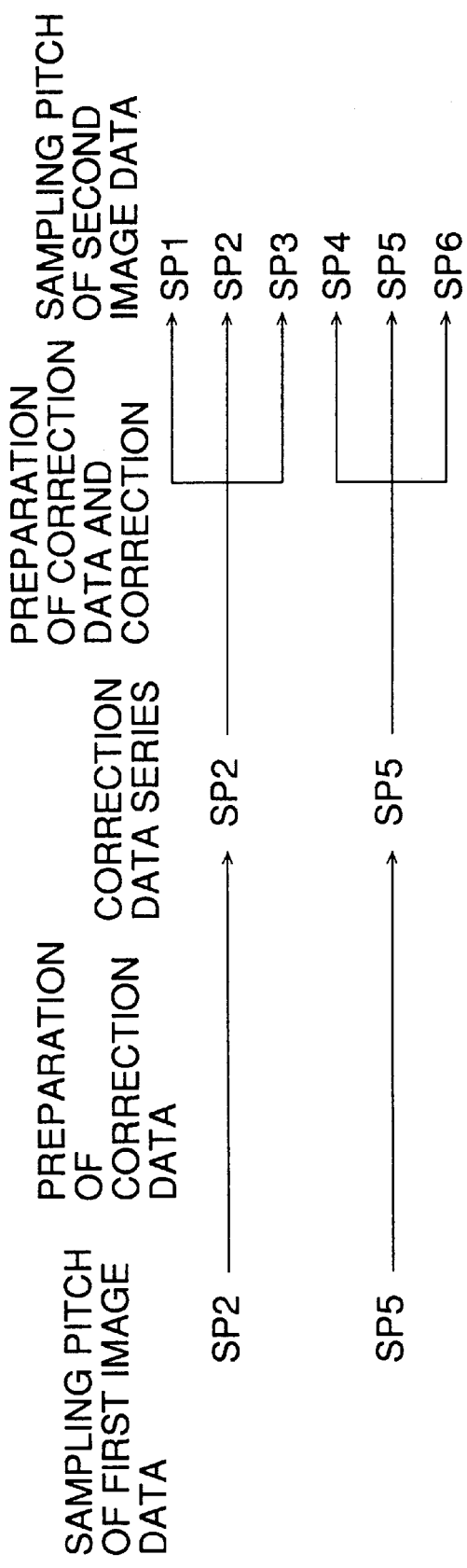
FIG. 11 is an illustration showing operations of another example wherein image information are obtained for a plurality of sampling pitches of the invention.

FIG. 11 is an illustration showing operations of another example wherein image information are obtained for a plurality of sampling pitches of the invention. In this case, when reading the first image information, SP2 and SP5 among sampling pitches SP1–SP6 are used for sampling to obtain the first image information, and correction data in the case of SP2 and SP5 respectively are prepared and stored. Then, when reading the second image information, the correction is made while preparing correction data in each of other sampling pitches SP1, SP3, SP4 and SP6.

In the case of the methods explained above, a control means is required to have a function for selecting a sampling pitch. When obtaining data of a different sampling pitch from image data of a certain sampling pitch, it is possible to use re-sampling methods used generally such as proximity approximation, linear interpolation and non-linear interpolation. Even in this example, it is possible to eliminate irregularity with no position repeatability by using optimum correction data in accordance with sampling pitches.

For example, with regard to streak-shaped irregularity caused by irregularity in polygon mirror surfaces, when a sampling pitch in the sub-scanning direction is smaller, an amount of feeding in the sub-scanning direction per one revolution of a polygon mirror is smaller, and therefore, the corresponding frequency components move to the higher frequency side. Therefore, it is preferable that characteristics of frequency processing are shifted to the high frequency side accordingly. To be concrete, it is preferable that a cut-off frequency (frequency wherein response is reduced by −3 dB) of low-pass filtering processing is set to a higher frequency side when a sampling pitch is smaller.

FIG. 12 represents illustrations each showing operations of an example wherein different frequency processing is performed depending on a sampling pitch of image information of the invention. Characteristics shown in (a) represent frequency spectrum of image information obtained when a sampling pitch is small. When the sampling pitch is small, components corresponding to streak-shaped irregularity appear in a high frequency band (P1 in the figure). Accordingly, a width of a passing band of a low-pass filter can be relatively wide as shown in (b) in the same figure. On the contrary, when the sampling pitch is large, frequency spectrum of image information obtained takes a form shown in (c) and components corresponding to streak-shaped irregularity appear in a low frequency band (P2 in the figure). To eliminate this component, therefore, a width of a band of a low-pass filter to be used needs to be narrower than that shown in (b). Characteristics of a low-pass filter in this case are shown in (d). In the present example, it is possible to prepare the optimum correction data depending on sampling pitches, by performing different frequency processings depending on sampling pitches.

One-dimensional correction data prepared based on one-dimensional irregularity information will be explained as follows.

Figure 21:
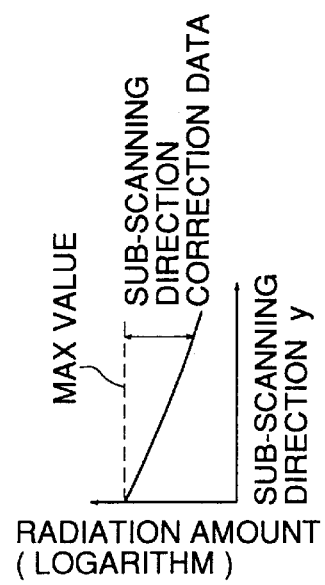
FIGS. 21(a) through 21(c) represent illustrations for methods of preparing correction data.
Figure 21:
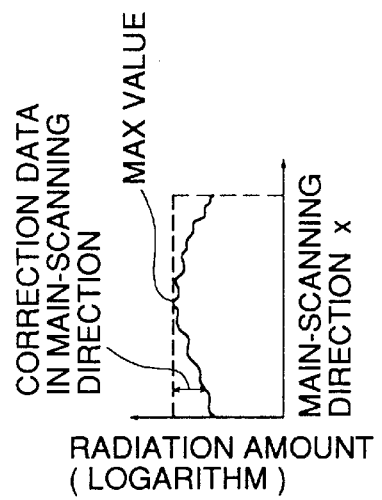
Figure 21:
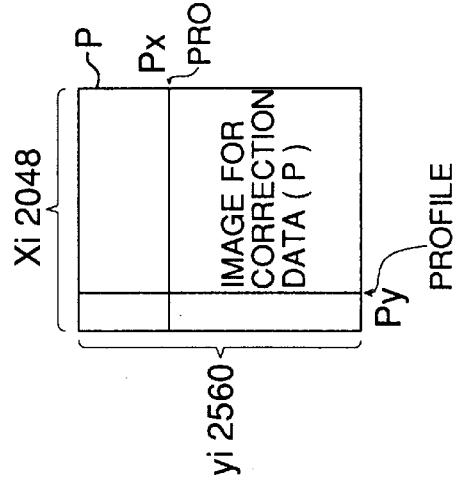

FIG. 21 represents illustrations showing an example of a method for preparing correction data mentioned above. In (a) of the figure, P is the first photographing image information, Px shows the main-scanning direction for the image, and Py shows the sub-scanning direction for the image. Incidentally, it is assumed that 2028 pixels are arranged in the main-scanning direction and 2,560 scanning lines exist in the sub-scanning direction.

Px indicates a profile in the main-scanning direction x and Py indicates a profile in the sub-scanning direction. In this case, correction data are caused to obtain the difference between the maximum value of an amount of radiations in each of Px and Py profiles and an amount of radiations of each pixel in the main-scanning direction x (in the case of Px) and in the sub-scanning direction y (in the case of Py). Owing to this, the difference between the maximum value of an amount of radiations in Px profile and an amount of radiations of each pixel in the main-scanning direction x serves as the first correction data for the main-scanning direction x of a radiographic image conversion panel as shown in (b), and thereby image data in the main-scanning direction can be corrected. Further, the difference between the maximum value of an amount of radiations in Py profile and an amount of radiations of each pixel in the sub-scanning direction y serves as the second correction data for the sub-scanning direction y of a radiographic image conversion panel as shown in (c), and thereby image data in the sub-scanning direction can be corrected.

Incidentally, it is also possible to obtain a difference between the minimum value of an amount of radiations in each of profiles Px and Py and an amount of radiations in each of pixels in the main-scanning direction and the sub-scanning direction, and thereby to make it to be correction data in each of the main-scanning direction and the sub-scanning direction.

Figure 22:
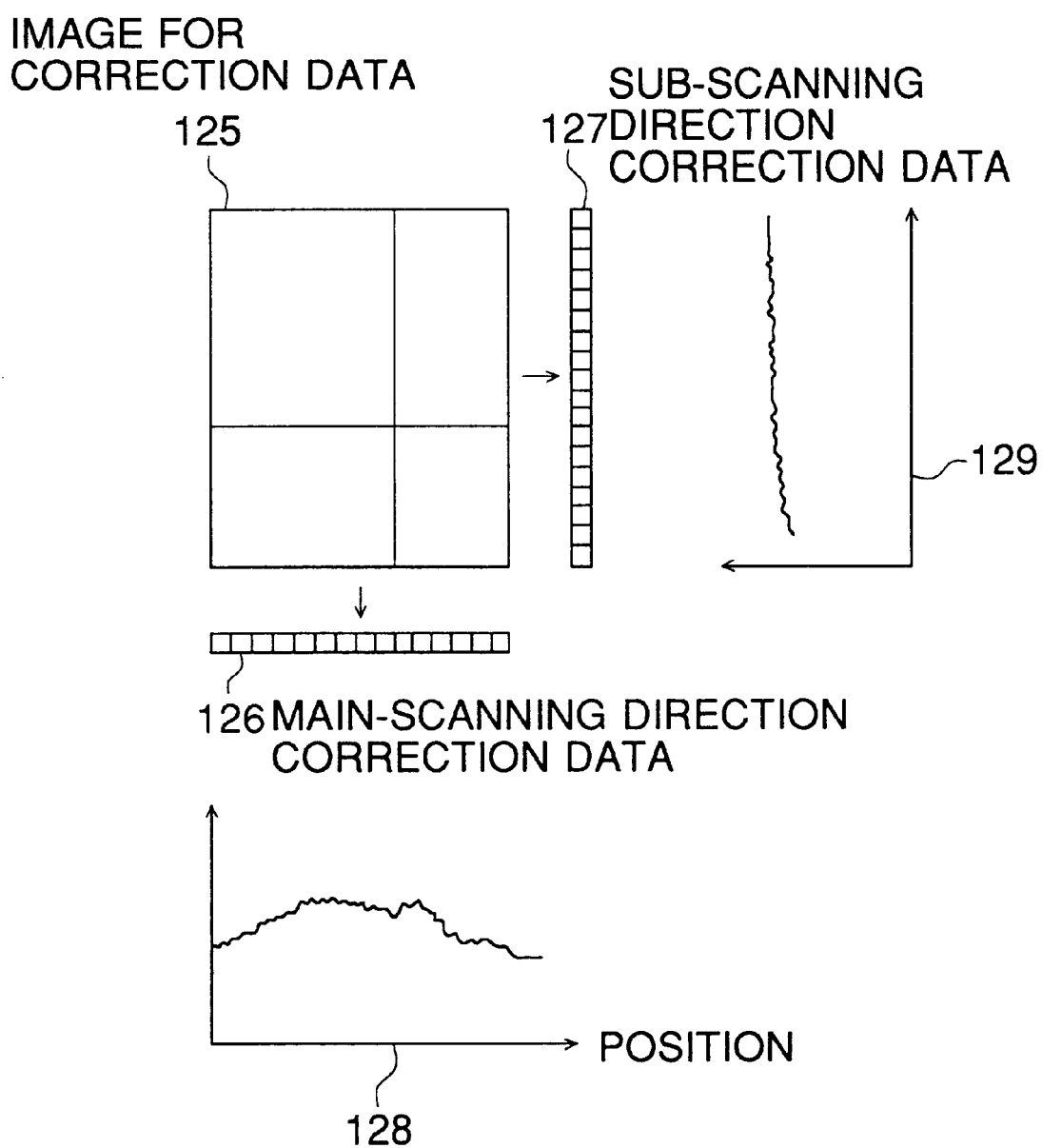
FIG. 22 is an illustration of correction data.

FIG. 22 represents illustrations of correction data. In the figure, the numeral 125 represents image information for correction data (image information read from a radiographic image conversion panel subjected to photographing under existence of no subject). Image profiles in the main-scanning direction and the sub-scanning direction of this image are shown respectively with 128 and 129. In the profiles 128 and 129, the axis of ordinate represents signals and the axis of abscissa represents positions. The numeral 126 represents correction data in the main-scanning direction prepared from image 125 for correction data, while, 127 represents correction data in the sub-scanning direction.

Figure 23:
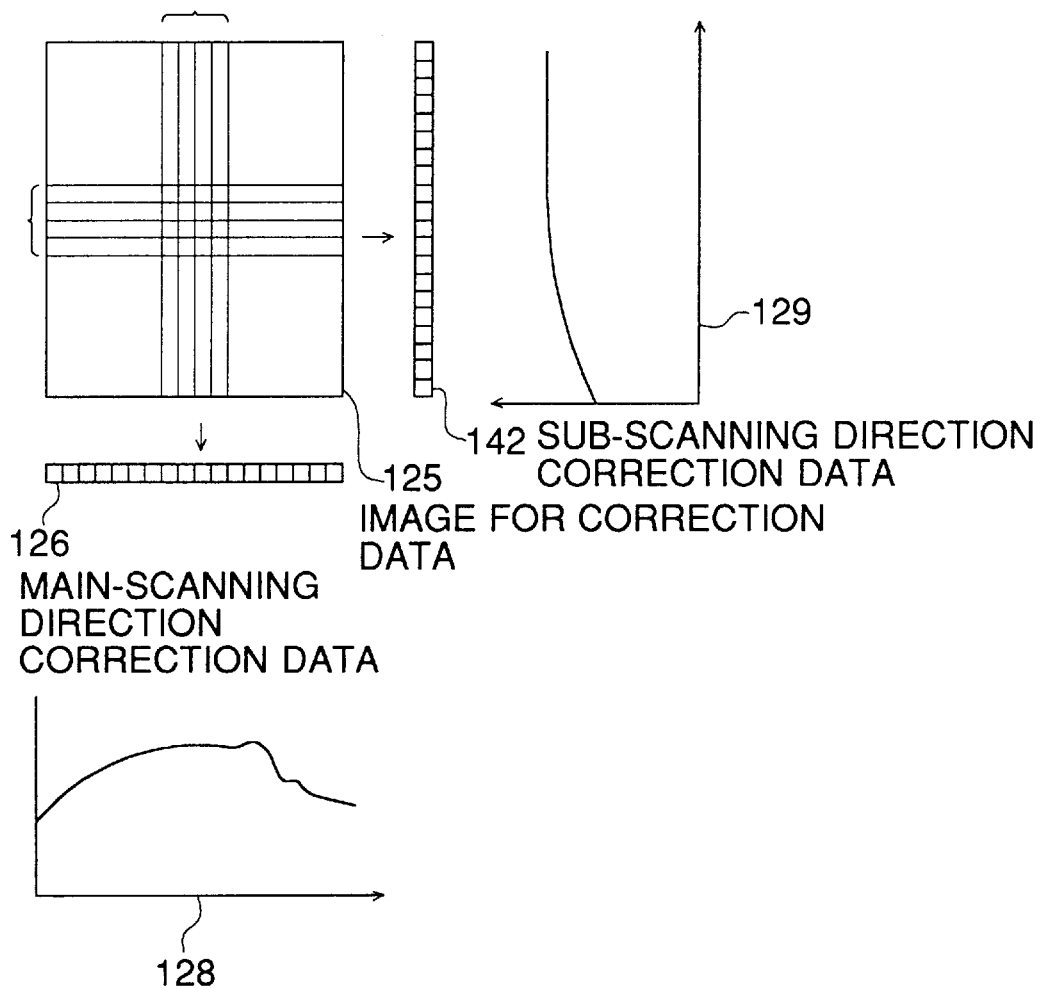
FIG. 23 is an illustration for another method of preparing correction data.

In the case of preparation of these correction data, if correction data are prepared from data of only one line or one row, values of correction data differ greatly from actual values when pulse-like noises are mixed. Therefore, as shown in FIG. 23 (the same items as those in FIG. 22 are given the same symbols), it is preferable to add photographing image information in the plural rows in main-scanning direction and then to obtain an average value thereof to make it to be correction data 126, in the case of correction data 126 in the main-scanning direction, for example. This applies also to the occasion of correction data in the sub-scanning direction.

For such correction, data of a corresponding pixel of correction data (same amount of correction for the same row) in the main-scanning direction can be added to data of an amount of radiations of each pixel on the same row of the second photographing image information (image information obtained from a radiographic image conversion panel subjected to photographing under existence of a subject), and data of a pixel on a corresponding scanning line of correction data (same amount of correction for the same scanning line) in the sub-scanning direction can be added to data of an amount of radiations of each pixel on the same scanning line (same row). Namely, in the example of correction wherein correction data in the main-scanning direction are used), image signal (S) is shown as follows because signals (s) are converted into logarithms.

$$(S)=\log s$$

When assuming that signal (s) is 0.7 times in the irregularity in the main-scanning direction, the following holds.

$$(S')=\log (s \times 0.7)=\log 0.7+\log s=\log s-0.15 \quad (22)$$

Therefore, if 0.15 which is the correction data in the main-scanning direction is added to obtained signal (S'), the sum serves as a corrected data of irregularity in the main-scanning direction. This applies exactly to the occasion of irregularity in the sub-scanning direction wherein correction data in the sub-scanning direction are used. Therefore, if the first correction data and the second correction data are added or each pixel, it is possible to obtain data wherein irregularity in the main-scanning direction and irregularity in the sub-scanning direction are corrected.

In this method, a memory area for storing correction data has only to be 2048+2560 at the best in the case of FIG. 21, and a memory capacity can be small accordingly. It is also possible to obtain composite correction data for a relevant pixel from correction data in the main-scanning direction and correction data in the sub-scanning direction in advance, and thereby to correct all pixels by the use of the composite correction data. It is further possible to prepare correction data for each group of plural pixels or for each group of plural scanning lines.

Next, the constitution of an apparatus for realizing the method of the invention will be explained as follows.

In this case, the constitution in the invention will be explained, referring to FIG. 13 and FIG. 14.

Figure 13:
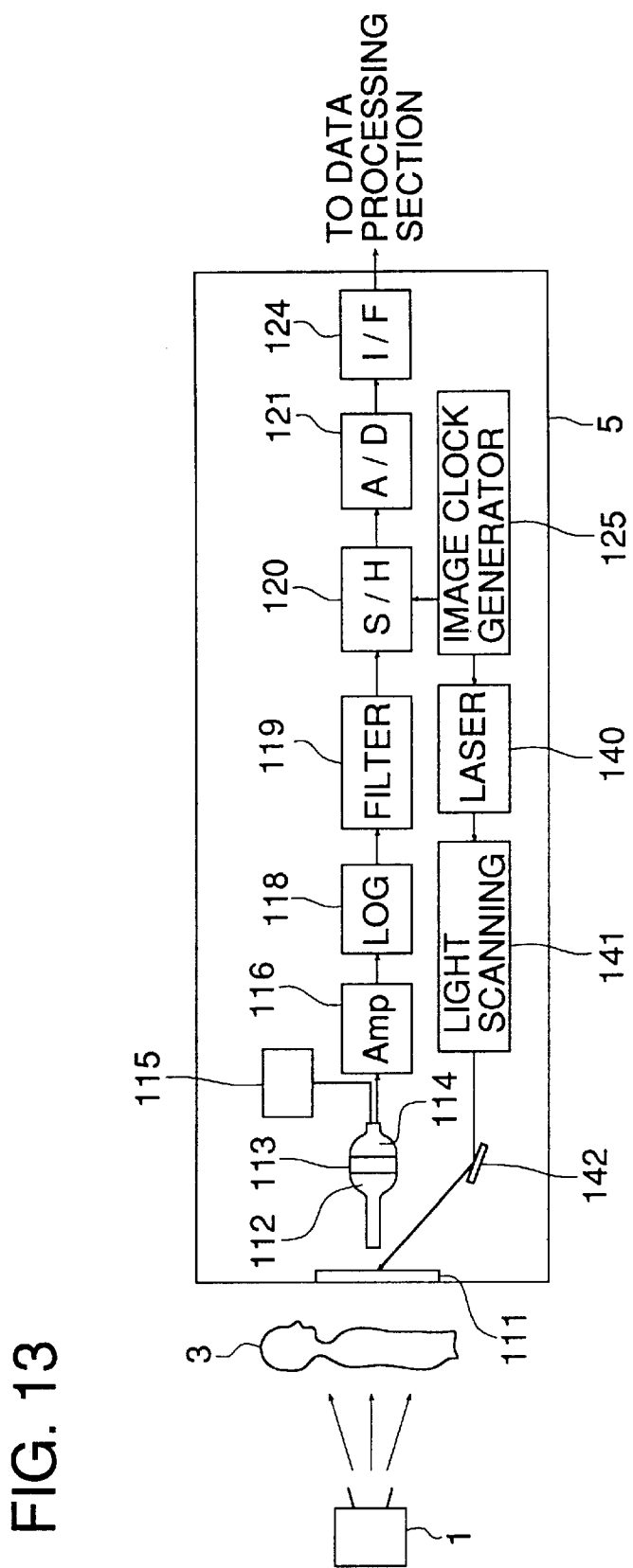
FIG. 13 is a structural block diagram showing an example of an image reading section used in the invention.
Figure 14:
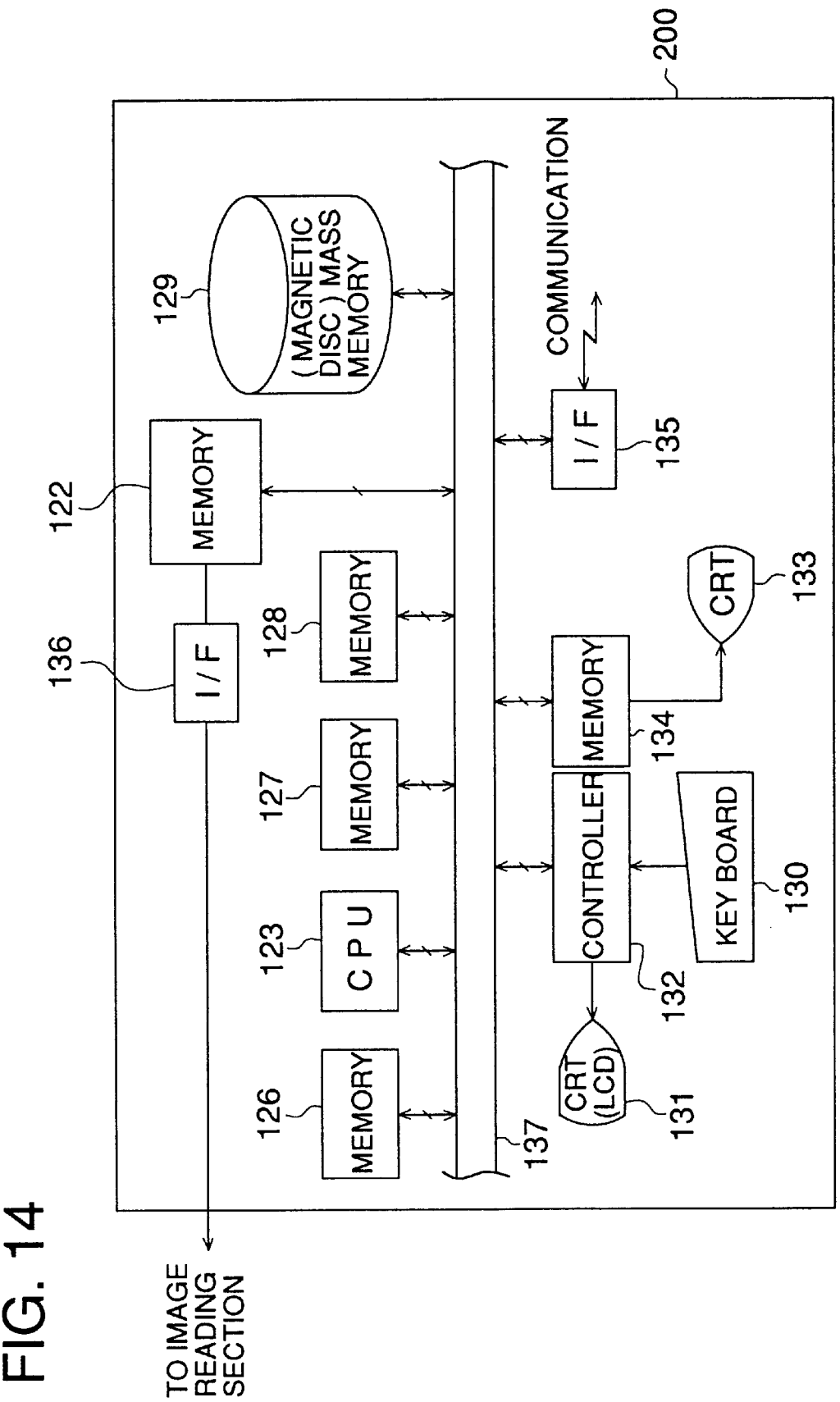
FIG. 14 is a structural block diagram showing an example of a data processing section used in the invention.
Figure 19:
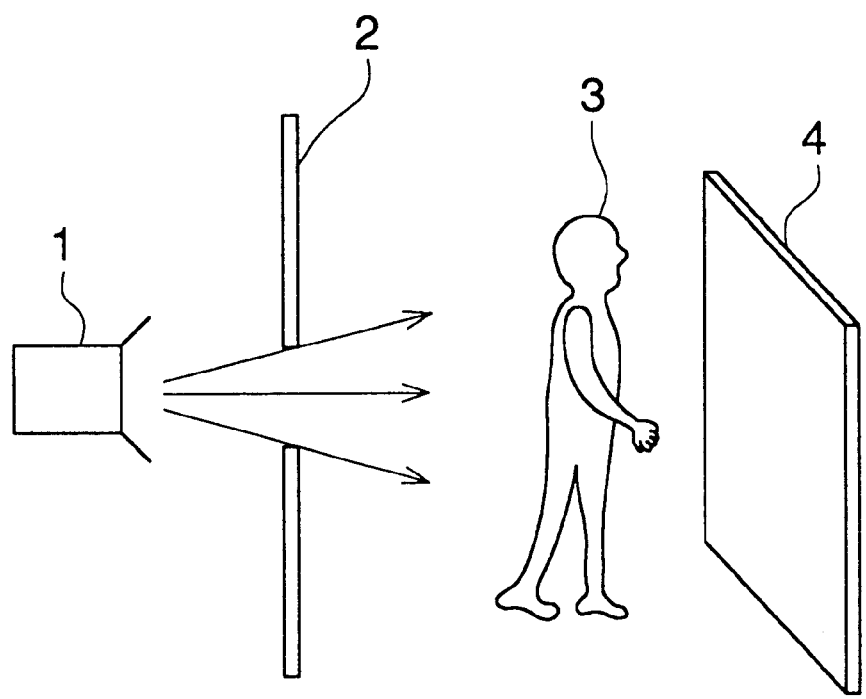
FIG. 19 is an illustration of image recording on a stimurable phosphor.
Figure 20:
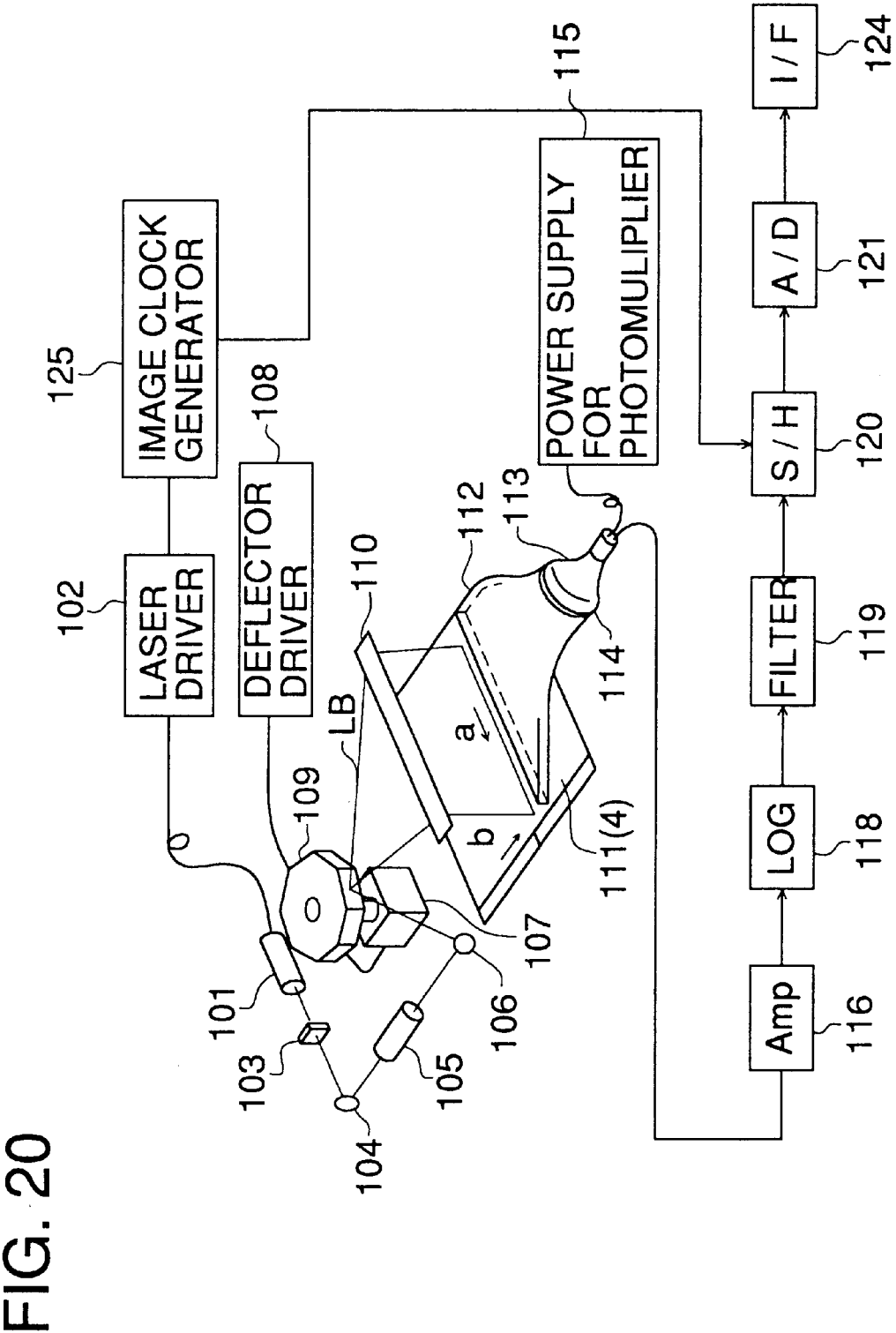
FIG. 20 is a block diagram showing an example of the constitution of a conventional apparatus.

FIG. 13 is a structural block diagram showing an example of an image reading section used in the invention, and FIG. 14 is a structural block diagram showing an example of a data section used in the invention, in which the same sections as those in FIGS. 19 and 20 are given the same symbols. In FIG. 13, panel 111 (radiographic image conversion panel) containing a stimurable phosphor is arranged to be fixed in the image reading section 5. The numeral 140 is a laser section that emits a laser beam in synchronization with output generated from image clock generator 125, and the numeral 141 is an optical scanning section serving as a laser optical system that receives a laser beam emitted from the laser section 140. Laser driver circuit 102 and semiconductor laser light source 101 in FIG. 20 are included in 141, and the optical scanning section 141 includes optical elements 103, 104, 105 and 106 in FIG. 20, while reflection section 142 includes deflector 107, deflector driver 108 and polygon mirror 109 in FIG. 20.

An X-ray emitted from X-ray source 1 under existence of no subject 3 or under existence of subject 3 enters radiographic image conversion panel 111 and forms on the radiographic image conversion panel 111 a latent image without or with subject 3. On the other hand, a laser beam emitted from the laser section 140 in sychronization with a clock is irradiated on the radiographic image conversion panel 111 from the reflection section 142 through the optical scanning section 141, so that accelerating radiation is caused from the radiographic image conversion panel 111. This accelerating radiation is converged by converging means 112, transmitted through filter 113 that transmits only an area of wavelength of accelerating radiation, and arrives at light detector 114 equipped with a photomultiplier to be converted to analogue electric signals (image signals). Image signals outputted from the light detector 114 pass through front end amplifier where they are voltage-amplified, then further pass through logarithmic amplifier 118, filter 119 and sample hold circuit 120 that holds the signals for a certain period of time in synchronization with image clock signals, then are converted by A/D converter 121 into digital signals, and are sent to data processing section 200 through interface 124.

In FIG. 14, the numeral 136 represents interface with image reading section 5, the numeral 122 represents a memory that stores temporarily image data sent from the image reading section 5 to the image processing section 200 at high speed, 126 represents a memory for storing the first read image information obtained by irradiating radiations to accelerating phosphor 4 without arranging subject 3, the numeral 127 represents a memory for storing correction data prepared based on the first image information stored in the memory 126, the numeral 128 represents a memory for storing the second image information obtained by irradiating radiations to accelerating phosphor 4 by arranging subject 3. The numeral 129 is a magnetic disk used as a mass memory. The numeral 123 is a CPU serving as a correction operation means that conducts preparation and processing of various correction data for the obtained image information and further conducts various controls. The numeral 130 is an operation key board, 131 is a display section for operation, and 132 is a controller that controls the key board 130 and the display section 131. The numeral 133 is a display section where an image is outputted, and 134 is a memory for storing image information to be outputted on the display section 133. The numeral 135 is an interface for communication for communicating with the outside. As the display sections 131 and 133, a CRT, for example, is used. The numeral 137 is a bus to which each constitutional block is connected, and it is composed of an address bus, a data bus and a control bus.

In the constitution mentioned above, the first image information obtained by irradiating radiations on radiographic image conversion panel 111 without arranging subject 3 is stored in memory 126. The first image information stored in the memory 126 is read by CPU 123, then, the operation processing shown in FIG. 21 (extracting one-dimensional irregularity information for the main-scanning direction and/or sub-scanning direction and preparing at least one list of one-dimensional correction data based on one-dimensional irregularity information in the aforesaid direction and a prescribed standard values) is performed, and a list of one-dimensional correction data for the main-scanning direction and/or a list of one-dimensional correction data for the sub-scanning direction of the radiographic image conversion panel 111 (a list of the first one-dimensional correction data) are prepared. The list of correction data thus prepared is stored in memory 127.

CPU 123 conducts spatial frequency processing that reduces spatial frequency components for the list of correction data in the main-scanning direction and/or sub-scanning direction stored in memory 127, then prepares the second list of one-dimensional correction data, and stores it in memory 127. Then, CPU 123 stores the second image information obtained by arranging subject 3 in memory 128, and corrects the second image information by the use of a list of one-dimensional correction data in the main-scanning direction and/or sub-scanning direction stored in memory 127. As a result, it is possible to conduct correction in the main-scanning direction and/or sub-scanning direction by the use of correction data from which frequency components corresponding to irregularity with no position repeatability have been reduced, thus it is possible to obtain accurate image information.

In this case, due to the aforesaid spatial frequency processing which is low-pass filtering processing, it is possible to eliminate effectively irregularity with no position repeatability containing high frequency components from correction data.

Further, due to the aforesaid spatial frequency processing which is band-cut filtering processing, it is possible to eliminate effectively irregularity with no position repeatability containing a prescribed low frequency components from correction data.

Further, due to the aforesaid spatial frequency processing which is simple average processing in the direction of a list of data, it is possible to eliminate irregularity with no position repeatability from correction data in a short processing time.

Further, due to the aforesaid spatial frequency processing which is weighted average processing in the direction of a list of data, it is possible to eliminate only irregularity with no position repeatability from correction data selectively.

Due to a cut-off frequency in the aforesaid low-pass filtering processing which is 0.5–2.0 cycle/mm, it is possible to eliminate further effectively the irregularity with no position repeatability caused by irregularity in an inclination angle of a polygon mirror and irregularity of reflection factor in mirror surfaces.

On the other hand, the second image information obtained by irradiating radiations on radiographic image conversion panel 111 by arranging subject 3 is stored in memory 128. After each prescribed data is stored in each memory 126, 127 or 128 in the aforesaid manner, CPU 123 conducts correction operation like that explained above for the second photographed image information stored in memory 128 by the use of correction data stored in memory 127.

Owing to the constitution mentioned above, it is possible to conduct correction in the main-scanning direction and/or sub-scanning direction by the use of correction data from which irregularity with no position repeatability has been eliminated. It is further possible to conduct correction which is close to two-dimensional total correction, using a memory of relatively small capacity, by conducting one-dimensional irregularity correction in the main-scanning direction and irregularity correction in the sub-scanning direction. For a series of photographing, it is possible to use an X-ray source that is used generally. Further, preparation of correction data can be performed at any time.

In this case, when the aforesaid reading section 5 obtains the first image information mentioned above for plural sampling pitches, aforesaid CPU 123 prepares plural lists of correction data based on the first image information, and thereby it is possible to correct irregularity using optimum correction data depending on sampling pitches, by selecting a list of correction data used for correction, depending on sampling pitches for obtaining the second image information.

Further, depending on sampling pitches of the first image information and/or sampling pitches of the second image information, CPU 123 can prepare the optimum correction data depending on sampling pitches by conducting different spatial frequency processing, in accordance with sampling pitches of the aforesaid first image information and/or the second image information.

Figure 15:
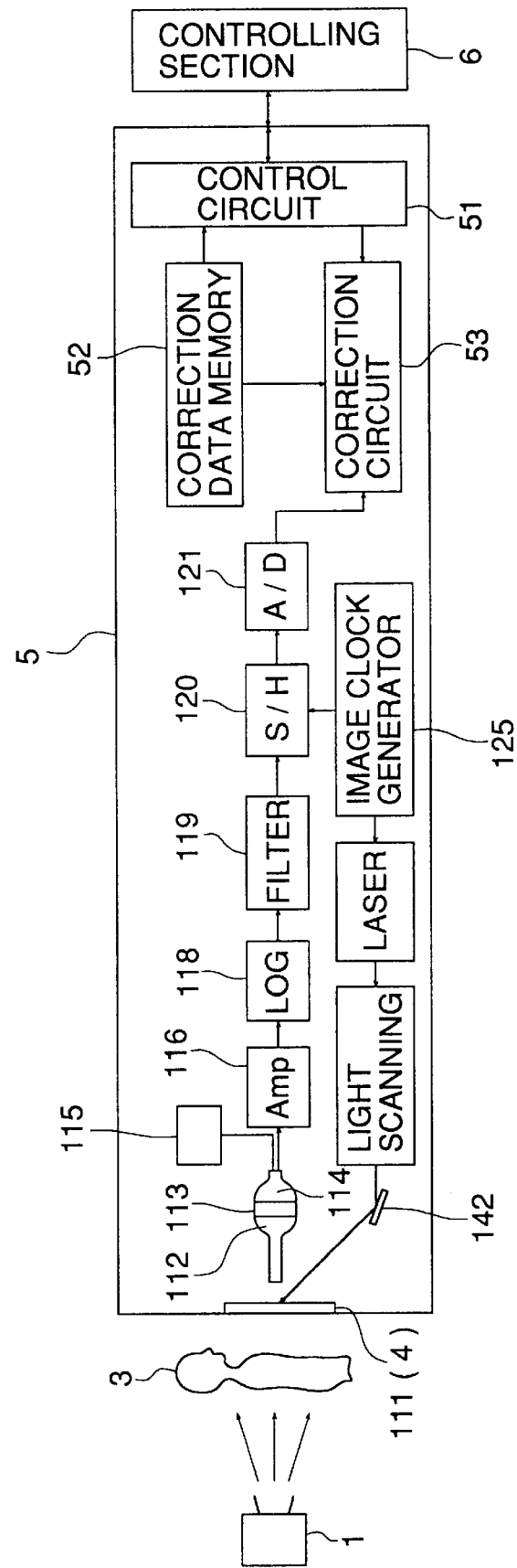
FIG. 15 is a structural block diagram showing another example of an image reading section used in the invention.

Although both preparation of correction data and correction operation are conducted by CPU 123 in the example mentioned above, it is also possible to conduct only preparation of correction data through CPU 123 and to provide a circuit for correction. A constitutional block diagram of primary parts in the aforesaid constitution is shown in FIG. 15 wherein the same parts as those in FIG. 13 are given the same symbols. In image reading section 5, there is provided control circuit 51 to which correction data memory 52 and correction circuit 53 are connected. Correction signals are added to the correction circuit 53 and correction data are added from the correction data memory 52 to the correction circuit 53. Control section 6 is connected to the image reading section 5 through the control circuit 51. The control section 6 controls operations of the image reading section 5 and prepares correction data. Though the control section 6 is provided independently outside the image reading section 5 in FIG. 15, it can also be provided in the image reading section 5. Incidentally, the control section 6 can be considered one wherein a portion for correcting irregularity in the main-scanning direction and irregularity in the sub-scanning direction is eliminated from a data processing apparatus shown in FIG. 14.

Figure 16:
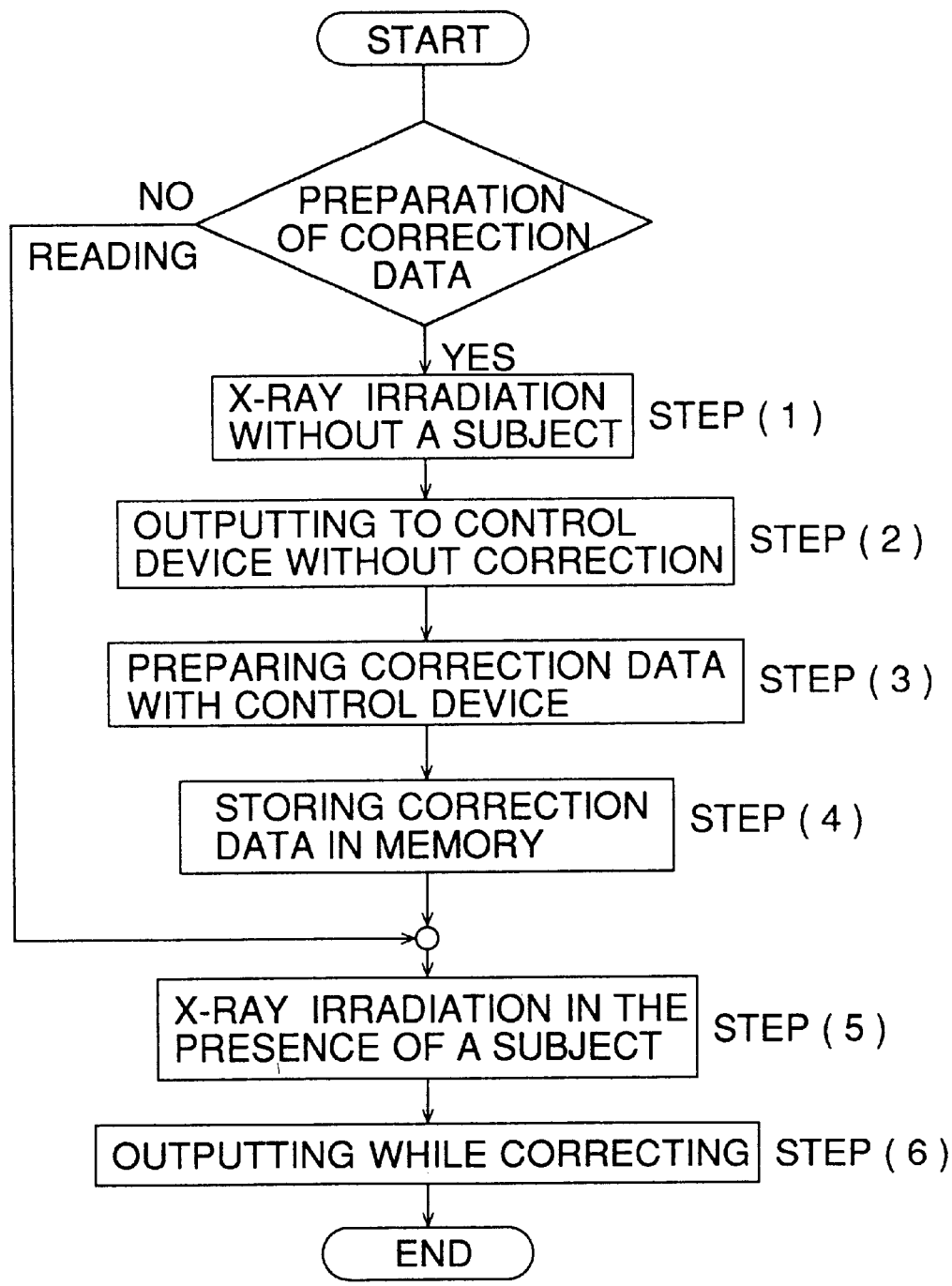
FIG. 16 is a flowchart showing operations of another example.

FIG. 16 is a flowchart showing the flow of operations in the case where the image reading section shown in FIG. 15 is used. When preparing correction data, X-ray is first irradiated without arranging a subject (Step (1)). The image obtained is outputted to the control section 6 without being corrected (Step (2)). The control section 6 prepares correction data based on the image inputted (Step (3)), and stores the correction data thus prepared in memory 52 (Step (4)).

When reading images, on the other hand, X-ray is irradiated with a subject arranged (Step (5)), and image data are outputted while correcting by the use of correction data stored in memory 52 (Step (6)). In this case, it is also possible that a non-volatile memory such as a magnetic disk or the like is provided in the control section 6, for example, so that correction data are stored at any time in advance, and they are transmitted to the image reading section 5 in the case of start-up of an apparatus.

In the illustration above, the image reading section 5 serves as the first image reading means and the second image reading means. However, the invention is not limited to this, and it can also take the constitution wherein a reading section is provided separately.

Figure 17:
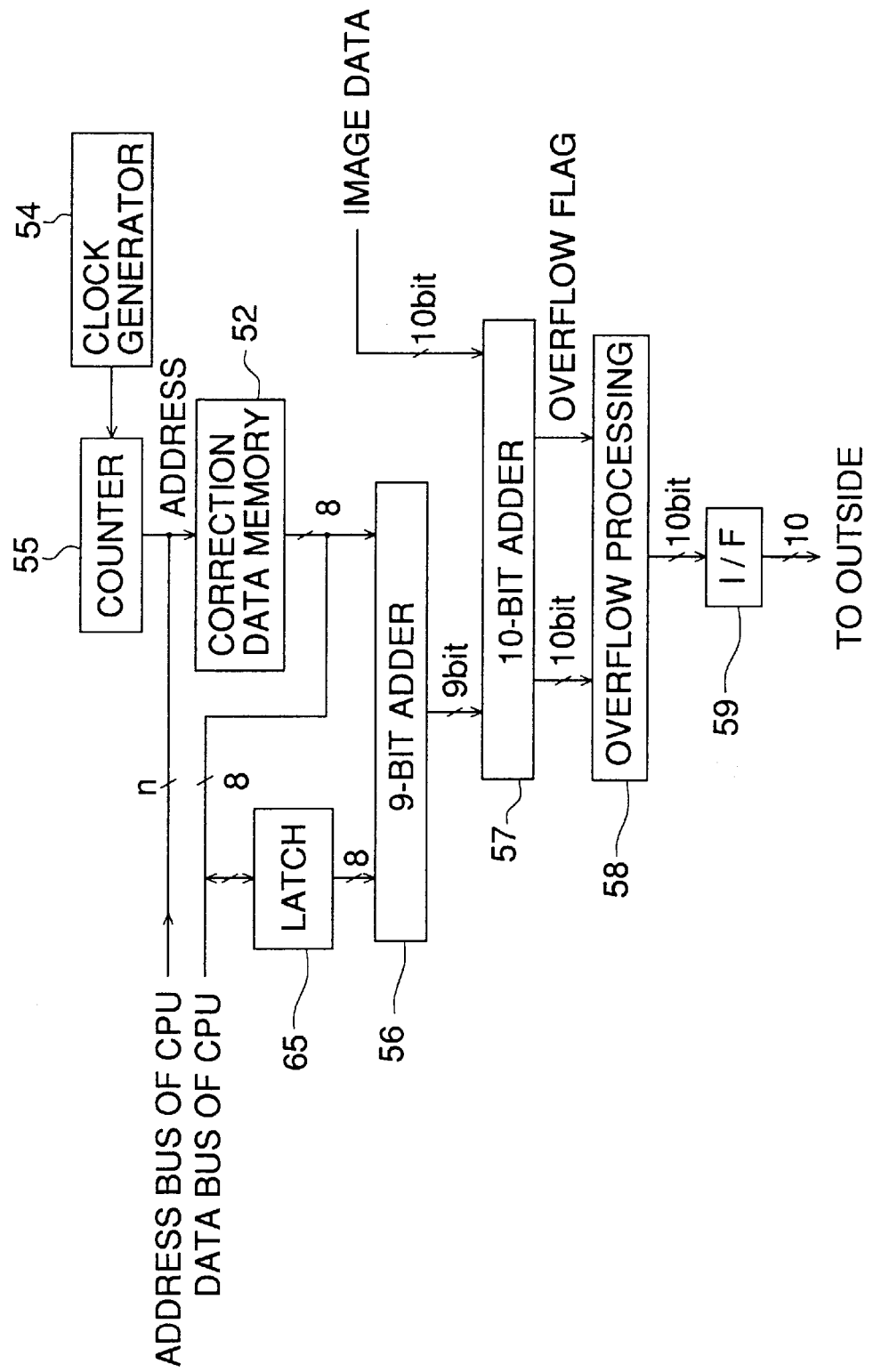
FIG. 17 is a block diagram showing an example of the structure of a digital correction circuit.

FIG. 17 is a block diagram showing an example of constitution of correction circuits which conduct correction in a digital manner. In this example, image data is 10 bits and it covers 3 digits. On the other hand, correction data are of 8-bit constitution for both irregularity in the main-scanning direction and irregularity in the sub-scanning direction. The reason for the 8-bit constitution is that 10-bit constitution causes the memory size to be too big and the irregularity in the main-scanning direction and irregularity in the sub-scanning direction of the actual image data are not so great and do not need 10-bit correction data. An 8-bit size is sufficient in practical use because it corresponds to an amount that covers ¾ digits. Thus, an employment of 8-bit needs only about a half of what is required in the case of 10-bit constitution in terms of digital circuits including memory capacity.

In FIG. 17, when preparing correction data, "0" is first written in correction data memory 52 and latch 65 from CPU. Then, an operation enters an action for reading image data actually. When reading image data, clocks corresponding to each pixel or plural pixels are added to counter 55 from clock generator 54. The counter 55 is subjected to increment by the aforesaid clock in synchronization with horizontal synchronization signals. In this case, correction data read from correction data memory 52 represent "0". Therefore, data outputted to the outside through 9-bit adder 56, 10-bit adder 57, over-flow processing circuit 58 and interface 59 serve as image data for preparing correction data for the irregularity in the main-scanning direction and irregularity in the sub-scanning direction. When correction data are written in, CPU receives correction data sent from a control section, and stores them in correction data memory 52.

When correcting image data, clocks are added from clock generator 54, in the same way as in the foregoing, to counter 55 which thereby is subjected to increment. To latch 65, correction data for irregularity in the main-scanning direction are read out and set by CPU from correction data memory 52 during the term when no image data are read within a period of one scanning cycle. Incidentally, these correction data may be set either plural times or only once. By executing the procedures mentioned above, it is possible to correct.

Figure 18:
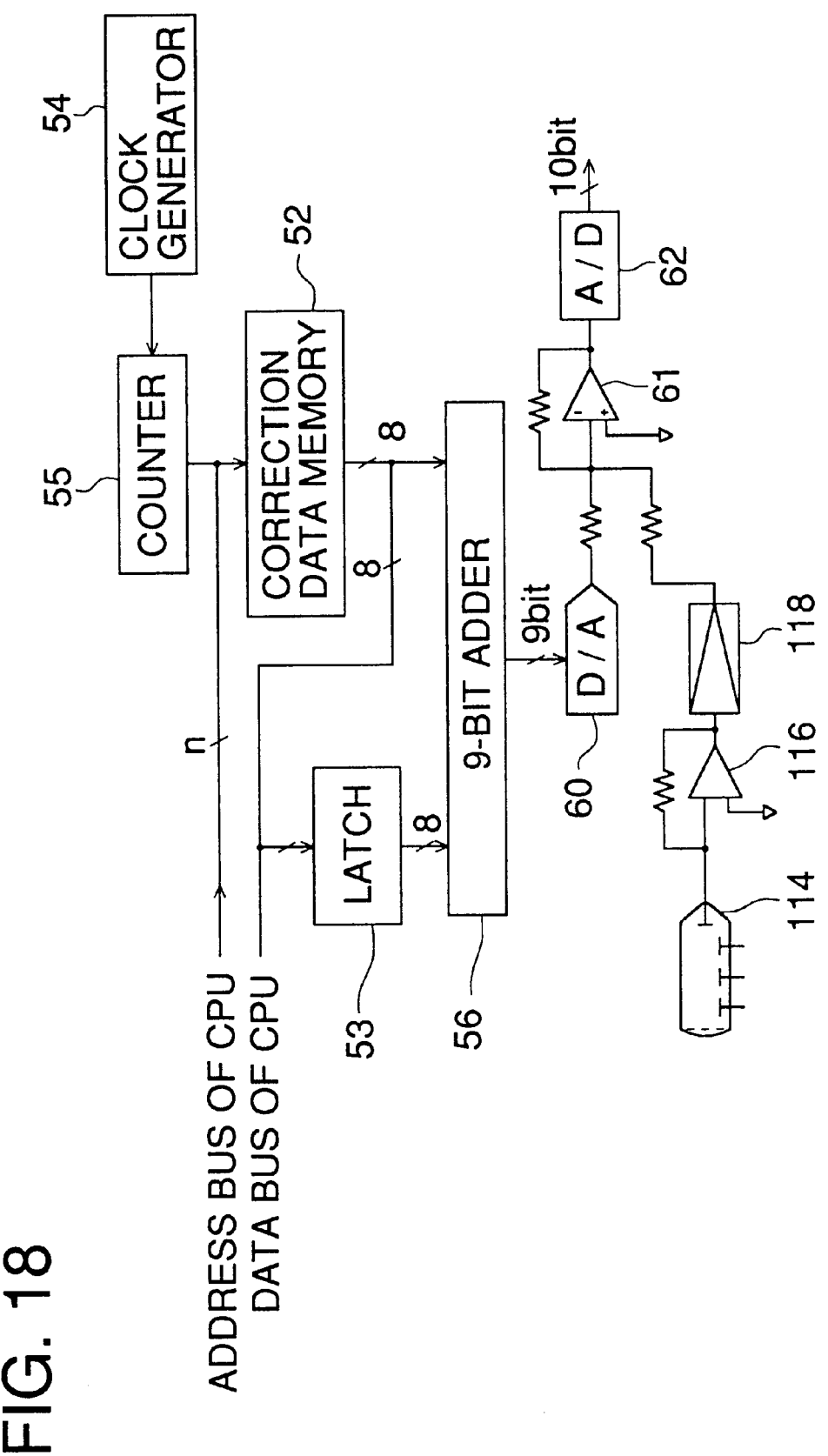
FIG. 18 is a block diagram showing an example of the constitution of an analogue correction circuit.

FIG. 18 is a diagram of a concrete example of a correction circuit that conducts correction in the case of analogue. In the constitution shown in FIG. 18, 9-bit correction data are added to D/A converter 60 to be converted to analogue signals, then added to image signals which are added to adder 61 to be logarithm-converted, and are converted by A/D converter 62 to 10-bit digital signals to be outputted.

In the above-mentioned description of the radiographic image information reading apparatus, there has been explained an example wherein lists of the first one-dimensional correction data equivalent to at least one list in the main-scanning direction and/or sub-scanning direction are prepared from the first image information, then, spatial frequency processing for reducing prescribed frequency components is performed for the lists of correction data, and then, lists of the second one-dimensional correction data equivalent to at least one list in the main-scanning direction and/or sub-scanning direction are prepared, and the second image information is corrected by the use of the lists of the second one-dimensional correction data.

However, the invention is not limited to the foregoing. For example, it is also possible to employ a method wherein spatial frequency processing for reducing prescribed spatial frequency components is conducted for at least one of the main-scanning direction and sub-scanning direction of image information with no subject to obtain and store image information, then, one-dimensional irregularity information are extracted for at least one of the main-scanning direction and sub-scanning direction for the image information mentioned above and a list of one-dimensional correction data equivalent to at least one list is prepared and stored based on one-dimensional irregularity information in the direction mentioned above and on prescribed standard values, and thereby image information obtained with a subject arranged are corrected by the use of the list of the one-dimensional correction data in the aforesaid direction. Owing to this, correction in the main-scanning direction and/or sub-scanning direction can be carried out by the use of correction data wherein frequency components corresponding to irregularity with no position repeatability have been reduced, and accurate image information can be obtained.

In the example mentioned above, there has been explained an example wherein a list of one-dimensional correction data is provided for each of the main-scanning direction and/or sub-scanning direction. However, an apparatus of the invention is not limited to this, and it is preferable that plural lists of one-dimensional correction data are provided for the main-scanning direction and/or sub-scanning direction, and each list of correction data is used properly for the right image area (see FIG. 2). Further, with regard to lists of one-dimensional correction data to be prepared for the main-scanning direction and/or sub-scanning direction, it is not necessary that correction data are prepared for all pixels, but it is sufficient that correction data are prepared for some pixels on a thinned-out basis. Under this condition, the memory capacity can further be made small.

Without being limited to the occasion where correction data are made to be lists of one-dimensional data for the main-scanning direction and/or sub-scanning direction, the invention makes it possible to conduct prescribed spatial frequency processing on image information obtained with no subject or on the image information subjected to prescribed processing, to obtain and store two-dimensional correction data corresponding to each pixel, and to correct signal values of each pixel by the aforesaid correction data for image information obtained with a subject, and thereby to obtain the image information. Owing to this, it is possible to eliminate irregularity with no position repeatability from correction data by reducing frequency components corresponding to irregularity with no position repeatability, and thereby to obtain accurate image information.

Incidentally, in the example mentioned above, spatial frequency processing is performed for both the main-scanning direction and the sub-scanning direction. However, it is not always necessary to perform for both directions. When there is a tendency that irregularity with no position repeatability occurs in the sub-scanning direction, frequency processing has only to be performed on image information, image information subjected to prescribed processing, or on the first one-dimensional correction data all in the sub-scanning direction. Thus, irregularity correction can be carried out by using correction data subjected to spatial frequency processing for the sub-scanning direction, and using correction data which are not subjected to spatial frequency processing for the main-scanning direction.

As stated in detail above, the first invention makes it possible to eliminate irregularity with no position repeatability effectively from correction data, because the correction data are obtained from those wherein spatial frequency processing that reduces prescribed spatial frequency components has been performed on the first image or the first image subjected to prescribed processing.

The second invention makes it possible to eliminate irregularity with no position repeatability effectively from correction data by obtaining the first correction data equivalent to at least one list from the first image information by extracting one-dimensional irregularity information for at least one of the main-scanning direction or the sub-scanning direction, and by obtaining the second one-dimensional correction data by performing spatial frequency processing that reduces prescribed spatial frequency components on the aforesaid correction data.

The third invention makes it possible to obtain the second image information by performing spatial frequency processing that reduces prescribed spatial frequency components for at least one of the main-scanning direction and the sub-scanning direction of the first image information, to extract one-dimensional irregularity information for at least one of the main-scanning direction or the sub-scanning direction for the second image information mentioned above, to prepare one-dimensional correction data equivalent to at least one list based on one-dimensional irregularity information in the aforesaid direction, and thereby to eliminate irregularity with no position repeatability effectively from correction data.

In the first invention, one-dimensional irregularity information for the main-scanning direction and the sub-scanning direction are extracted for the aforesaid first image information, then, first one-dimensional correction data are prepared based on one-dimensional irregularity information for each of the main-scanning direction and the sub-scanning direction, and different spatial frequency processing is performed for each of the first one-dimensional correction data in the main-scanning direction and the first one-dimensional correction data in the sub-scanning direction. Owing to this, it is possible to eliminate irregularity with no position repeatability for each of the main-scanning direction and the sub-scanning direction from correction data effectively.

In the second invention, the aforesaid first image information or the aforesaid first image information on which prescribed processing has been performed is subjected to spatial frequency processing which is different between the main-scanning direction and the sub-scanning direction. Owing to this, it is possible to eliminate irregularity with no position repeatability from correction data effectively, depending on the scanning direction.

In the third invention, the aforesaid first image information is subjected to spatial frequency processing which is different between the main-scanning direction and the sub-scanning direction. Owing to this, it is possible to eliminate irregularity with no position repeatability from correction data effectively, depending on the scanning direction.

It is characterized that the aforesaid spatial frequency processing is low-pass filtering processing. Owing to this, it is possible to eliminate irregularity with no position repeatability from correction data effectively, when the irregularity with no position repeatability represents high frequency components.

It is characterized that the aforesaid spatial frequency processing is band-cut filtering processing. Owing to this, it is possible to eliminate irregularity with no position repeatability from correction data effectively, when the irregularity with no position repeatability contains prescribed frequency components.

It is characterized that the aforesaid spatial frequency processing is simple average processing in the direction of a list of data. Owing to this, it is possible to eliminate irregularity with no position repeatability from correction data effectively within a short processing time.

It is characterized that the aforesaid spatial frequency processing is weighted average processing in the direction of a list of data. Owing to this, it is possible to eliminate only irregularity with no position repeatability from correction data selectively.

It is further characterized that the cut-off frequency in the aforesaid low-pass filtering processing is 0.5–2.0 cycles/mm. Owing to this, it is possible to eliminate effectively from correction data the irregularity with no position repeatability caused by irregularity in an inclination angle of a polygon mirror and irregularity of reflection factor in mirror surfaces.

It is further characterized in the first invention that the aforesaid first image information is obtained corresponding to plural sampling pitches, the correction data are obtained by performing spatial frequency processing on the plural first image information or on the first image information subjected to prescribed processing, and the correction data used for correction are selected corresponding to sampling pitches used in obtaining aforesaid second image information. Owing to this, it is possible to eliminate effectively the irregularity with no position repeatability from correction data depending on a sampling pitch.

It is further characterized in the second invention that the aforesaid first image information is obtained corresponding to plural sampling pitches, then lists of aforesaid first one-dimensional correction data based on each of the plural first image information are prepared, then lists of the second one-dimensional correction data corresponding to aforesaid lists of first one-dimensional correction data are prepared, and the lists of the second one-dimensional correction data used for correction are selected depending on sampling pitches used in obtaining aforesaid third image information. Owing to this, it is possible to eliminate effectively the irregularity with no position repeatability from correction data depending on a sampling pitch.

It is further characterized in the third invention that the aforesaid first image information is obtained corresponding to plural sampling pitches, then aforesaid second image information is prepared based on each of the plural first image information, then, a list of aforesaid one-dimensional correction data corresponding to the second image information is prepared, and a list of the one-dimensional correction data used for correction is selected depending on a sampling pitch used in obtaining aforesaid third image information. Owing to this, it is possible to eliminate effectively the irregularity with no position repeatability from correction data depending on a sampling pitch.

It is further characterized in the first and second inventions that different spatial frequency processing is performed depending on a sampling pitch for aforesaid first image information and/or a sampling pitch for aforesaid second image information. Owing to this, it is possible to eliminate effectively the irregularity with no position repeatability from correction data depending on a sampling pitch.

It is further characterized in the third invention that different spatial frequency processing is performed depending on a sampling pitch for aforesaid first image information and/or a sampling pitch for aforesaid third image information. Owing to this, it is possible to eliminate effectively the irregularity with no position repeatability from correction data depending on a sampling pitch.

Since correction data are obtained by the first correction operation means from those wherein spatial frequency processing that reduces prescribed spatial frequency components is performed on the first image or on the first image subjected to prescribed processing in the fourth invention, it is possible to eliminate effectively the irregularity with no position repeatability from correction data.

Since the first correction operation means obtains the first correction data equivalent to at least one list by extracting one-dimensional irregularity information for at least one of the main-scanning direction or the sub-scanning direction from the first image information, and the second correction operation means obtains the second one-dimensional correction data by performing spatial frequency processing that reduces prescribed spatial frequency components on aforesaid first correction data in the fifth invention, it is possible to eliminate effectively the irregularity with no position repeatability from correction data.

Since the first correction operation means obtains the second image information by performing spatial frequency processing that reduces prescribed spatial frequency components for at least one of the main-scanning direction and the sub-scanning direction of the first image information, and the second correction operation means extracts one-dimensional irregularity information for at least one of the main-scanning direction or the sub-scanning direction and thereby prepares one-dimensional correction data equivalent to at least one list based on one-dimensional irregularity information in aforesaid direction in the sixth invention, it is possible to eliminate effectively the irregularity with no position repeatability from correction data.

It is characterized in the fifth invention that aforesaid correction operation means extracts one-dimensional irregularity information for the main-scanning direction and the sub-scanning direction of aforesaid first image information and prepares the first one-dimensional correction data based on one-dimensional irregularity information in the main-scanning direction and the sub-scanning direction, and then, aforesaid second correction operation means performs different spatial frequency processing for the first one-dimensional correction data in the main-scanning direction and that in the sub-scanning direction. Owing to this, it is possible to eliminate effectively the irregularity with no position repeatability from correction data.

It is characterized in the fourth invention that aforesaid first correction operation means performs different spatial frequency processing for aforesaid first image information or aforesaid first image information subjected to processing, depending on the main-scanning direction or the sub-scanning direction. Owing to this, it is possible to eliminate effectively the irregularity with no position repeatability from correction data, depending on the scanning direction.

It is further characterized in the sixth invention that aforesaid first correction operation means performs different spatial frequency processing for aforesaid first image information, depending on the main-scanning direction or the sub-scanning direction. Owing to this, it is possible to eliminate effectively the irregularity with no position repeatability from correction data, depending on the scanning direction.

It is characterized that aforesaid spatial frequency processing is low-pass filtering processing. When irregularity with no position repeatability represents high frequency components, it can be eliminated effectively from correction data.

It is further characterized that aforesaid spatial frequency processing is band-cut filtering processing. Owing to this, when irregularity with no position repeatability contains prescribed frequency components, it can be eliminated effectively from correction data.

It is further characterized that aforesaid spatial frequency processing is simple average processing in the direction of a list of data. Owing to this, it is possible to eliminate effectively irregularity with no position repeatability from correction data in a short operation time.

It is further characterized that aforesaid spatial frequency processing is weighted average processing in the direction of a list of data. Owing to this, it is possible to eliminate selectively only irregularity with no position repeatability from correction data.

It is further characterized that the cut-off frequency in the aforesaid low-pass filtering processing is 0.5–2.0 cycles/mm. Owing to this, it is possible to eliminate effectively from correction data the irregularity with no position repeatability caused by irregularity in an inclination angle of a polygon mirror and irregularity of reflection factor in mirror surfaces.

It is further characterized in the fourth invention that aforesaid first image information reading means obtains aforesaid first image information for plural sampling pitches, aforesaid first correction operation means prepares a list of correction data corresponding to each of aforesaid plural first image information, and aforesaid second correction operation means selects a list of correction data used for correction in accordance with sampling pitches used in obtaining the second image information. Owing to this, it is possible to eliminate effectively the irregularity with no position repeatability from correction data depending on a sampling pitch.

It is further characterized in the fifth invention that aforesaid first image information reading means obtains aforesaid first image information for plural sampling pitches, aforesaid first correction operation means prepares a list of first one-dimensional correction data corresponding to each of aforesaid plural first image information, aforesaid second correction operation means prepares a list of second one-dimensional correction data corresponding to the list of the first one-dimensional correction data, and aforesaid third correction operation means selects a list of the second one-dimensional correction data used for correction in accordance with sampling pitches used in obtaining the second image information. Owing to this, it is possible to eliminate effectively the irregularity with no position repeatability from correction data depending on a sampling pitch.

It is further characterized in the sixth invention that aforesaid first image information reading means obtains aforesaid first image information for plural sampling pitches, aforesaid first correction operation means prepares the second image information corresponding to each of aforesaid plural first image information, aforesaid second correction operation means prepares a list of one-dimensional correction data based on the second image information, and aforesaid third correction operation means selects a list of the second one-dimensional correction data used for correction in accordance with sampling pitches used in obtaining the second image information. Owing to this, it is possible to select a list of optimum correction data corresponding to sampling pitches and to eliminate effectively the irregularity with no position repeatability from correction data.

It is further characterized that different spatial frequency processing is performed, depending on a sampling pitch of aforesaid first image information and/or that of aforesaid second image information. Owing to this, it is possible to eliminate effectively the irregularity with no position repeatability from correction data depending on a sampling pitch.

It is further characterized that different spatial frequency processing is performed, depending on a sampling pitch of aforesaid first image information and/or that of aforesaid third image information. Owing to this, it is possible to eliminate effectively the irregularity with no position repeatability from correction data depending on a sampling pitch.

As stated above, the invention makes it possible to eliminate irregularity with no position repeatability from correction data effectively, and thereby provides a radiographic image information reading method and a radiographic image information reading apparatus both being capable of correcting irregularity effectively, which offers great effects in practical use.

What is claimed is:

1. A radiographic image reading apparatus, comprising:
   (i) means for obtaining first image information, the first image information obtaining means including:
      means for scanning exciting light on a stimulable phosphor sheet which is irradiated with radiation without having a subject placed before it, and
      means for reading light emitted from the excited stimulable phosphor sheet so as to form the first image information, said first image information comprising image signals in a two dimensional form of pixels and having various spatial frequencies;
   (ii) means for obtaining correction data, the correction data obtaining means including:
      means for conducting a spatial frequency processing for reducing a predetermined spatial frequency component of the first image information, said predetermined spatial frequency component corresponding to an irregularity with poor reproducibility in terms of its position on the first image information, and
      means for forming the correction data from the first image information subjected to the spatial frequency processing in a manner such that an irregularity which is reproducible in terms of position on the first image information is eliminated from the correction data;
   (iii) means for obtaining second image information, the second image information obtaining means including:
      means for scanning exciting light on a stimulable phosphor sheet which is irradiated with radiation through a subject, and
      means for reading light emitted from the excited stimulable phosphor sheet so as to form the second image information, said second image information containing a radiographic image and comprising image signals; and
   (iv) means for correcting the image signals of the second image information using the correction data so as to obtain corrected image information containing the radiographic image,
   wherein the first and second image information obtaining means have plural types of selectable sampling pitch so that plural types of first image information are obtained,
   wherein the correction data obtaining means conducts the spatial frequency processing for each of the plural types of the first image information and prepares plural types of correction data corresponding to the plural types of the first image information, and
   wherein the correcting means utilizes respective ones of the plural types of the correction data in accordance with a sampling pitch selected by the second image information obtaining means.

2. The apparatus of claim 1, wherein the correction data obtaining means conducts a different spatial frequency processing for each of the plural types of the first image information.

3. An apparatus for reading a radiographic image on a stimulable phosphor sheet, comprising:
   (i) means for obtaining first image information, the first image information obtaining means including:
      means for scanning exciting light on the stimulable phosphor sheet which is irradiated with radiation without placing a subject before it, and
      means for reading light emitted from the excited stimulable phosphor sheet so that the first image information is composed of image signals in a two dimensional form of pixels and has various spatial frequencies;
   (ii) means for obtaining correction data, the correction data obtaining means including:
      means for conducting a spatial frequency processing for reducing a predetermined spatial frequency component of the first image information, the predetermined spatial frequency component corresponding to an irregularity with poor reproducibility in terms of its position on the first image information, and means for making the correction data to eliminate an irregularity which is reproducible of its position on the first image information;

(iii) means for obtaining second image information, the second image information obtaining means including:

means for irradiating a subject placed before the stimulable phosphor sheet with radiation so that a radiographic image corresponding to the subject is formed on the stimulable phosphor sheet, means for scanning the irradiated stimulable phosphor sheet with exciting light, and means for reading light emitted from the excited stimulable phosphor sheet so that the second image information containing the radiographic image is composed of image signals; and (iv) means for correcting the image signals of the second image information with the correction data and obtaining corrected image information containing the radiographic image;

wherein the first and second image information obtaining means have plural types of selectable sampling pitch so that plural types of first image information are obtained, the spatial frequency processing is conducted for each of the plural types of the first image information, plural types of the correction data corresponding to the plural types of the first image information are prepared, and one of the plural types of the correction data is used by the correcting means in accordance with a sampling pitch selected by the second image information obtaining means.

4. The method of claim 3, wherein a different spatial frequency processing is conducted for each of the plural types of the first image information.

* * * * *